(12) United States Patent
Serrero

(10) Patent No.: US 8,007,997 B2
(45) Date of Patent: *Aug. 30, 2011

(54) METHODS AND COMPOSITIONS FOR INHIBITING THE GROWTH OF HEMATOPOIETIC MALIGNANT CELLS

(75) Inventor: Ginette Serrero, Ellicott City, MD (US)

(73) Assignee: A&G Pharmaceutical, Inc., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/420,676

(22) Filed: Apr. 8, 2009

(65) Prior Publication Data

US 2010/0021475 A1    Jan. 28, 2010

Related U.S. Application Data

(60) Continuation of application No. 10/321,587, filed on Dec. 18, 2002, now abandoned, which is a continuation-in-part of application No. 09/456,886, filed on Dec. 8, 1999, now Pat. No. 6,720,159, which is a division of application No. 08/991,862, filed on Dec. 16, 1997, now Pat. No. 6,309,826, which is a continuation-in-part of application No. 08/863,079, filed on May 23, 1997, now abandoned.

(51) Int. Cl.
*C12Q 1/00* (2006.01)
*G01N 33/53* (2006.01)

(52) U.S. Cl. .............................. 435/4; 435/7.1; 435/7.23

(58) Field of Classification Search .................. None
See application file for complete search history.

*Primary Examiner* — Misook Yu
*Assistant Examiner* — Lei Yao
(74) *Attorney, Agent, or Firm* — Womble Carlyle Sandridge & Rice, PLLC

(57) ABSTRACT

Disclosed herein are compositions and methods for reducing the growth of hematopoietic malignant cells (e.g., B-cell leukemia cells). The methods involve reducing the growth of hematopoietic malignant cells by contacting hematopoietic malignant cells with GP88 antagonists. GP88 is an 88 KDa autocrine growth factor that promotes the growth of hematopoietic malignant cells. Antagonists to GP88 are provided which inhibit its expression or biological activity. The antagonists include antisense oligonucleotides and antibodies. Also provided are methods for determining if a patient is responding or is responsive to anti-cancer therapy (e.g., glucocorticoid therapy). Increased levels of GP88 in hematopoietic cells indicates a patient is not responding or responsive to anti-cancer therapy.

6 Claims, 33 Drawing Sheets

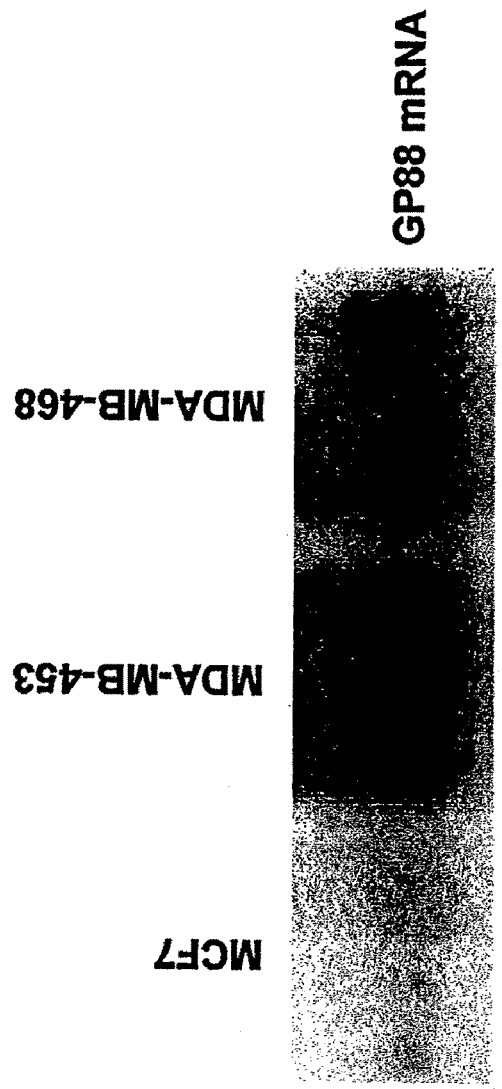

Mouse GP88 cDNA

| | | | | | | | | | | | | | | | |
|---|---|---|---|---|---|---|---|---|---|---|---|---|---|---|---|
| C | GGA | CCC | CGA | CGC | AGA | CAG | ACC | ATG | TGG | GTC | CTG | ATG | AGC | TGG | CTG | 46 |
| | | | | | | | | M | W | V | L | M | S | W | L | 8 |

GCC TTC GCG GCA GGG CTG GTA GCC GGA ACA CAG TGT CCA GAT GGG CAG  94
 A   F   A   A   G   L   V   A   G   T   Q   C   P   D   G   Q   24

TTC TGC CCT GTT GCC TGC TGC CTT GAC CAG GGA GGA GCC AAC TAC AGC  142
 F   C   P   V   A   C   C   L   D   Q   G   G   A   N   Y   S    40

TGC TGT AAC CCT CTT CTG GAC ACA TGG CCT AGA ATA ACG AGC CAT CAT  190
 C   C   N   P   L   L   D   T   W   P   R   I   T   S   H   H    56

CTA GAT GGC TCC TGC CAG ACC CAT GGC CAC TGT CCT GCT GGC TAT TCT  238
 L   D   G   S   C   Q   T   H   G   H   C   P   A   G   Y   S    72

TGT CTT CTC ACT GTG TCT GGG ACT TCC AGC TGC TGC CCG TTC TCT AAG  286
 C   L   L   T   V   S   G   T   S   S   C   C   P   F   S   K    88

GGT GTG TCT TGT GGT GAT GGC TAC CAC TGC TGC CCC CAG GGC TTC CAC  334
 G   V   S   C   G   D   G   Y   H   C   C   P   Q   G   F   H   104

TGT AGT GCA GAT GGG AAA TCC TGC TTC CAG ATG TCA GAT AAC CCC TTG  382
 C   S   A   D   G   K   S   C   F   Q   M   S   D   N   P   L   120

GGT GCT GTC CAG TGT CCT GGG AGC CAG TTT GAA TGT CCT GAC TCT GCC  430
 G   A   V   Q   C   P   G   S   Q   F   E   C   P   D   S   A   136

ACC TGC TGC ATT ATG GTT GAT GGT TCG TGG GGA TGT TGT CCC ATG CCC  478
 T   C   C   I   M   V   D   G   S   W   G   C   C   P   M   P   152

CAG GCC TCT TGC TGT GAA GAC AGA GTG CAT TGC TGT CCC CAT GGG GCC  526
 Q   A   S   C   C   E   D   R   V   H   C   C   P   H   G   A   168

TCC TGT GAC CTG GTT CAC ACA CGA TGC GTT TCA CCC ACG GGC ACC CAC  574
 S   C   D   L   V   H   T   R   C   V   S   P   T   G   T   H   184

ACC CTA CTA AAG AAG TTC CCT GCA CAA AAG ACC AAC AGG GCA GTG TCT  622
 T   L   L   K   K   F   P   A   Q   K   T   N   R   A   V   S   200

TTG CCT TTT TCT GTC GTG TGC CCT GAT GCT AAG ACC CAG TGT CCC GAT  670
 L   P   F   S   V   V   C   P   D   A   K   T   Q   C   P   D   216

FIG.8A

Mouse GP88 cDNA (continued)

```
GAT TCT ACC TGC TGT GAG CTA CCC ACT GGG AAG TAT GGC TGC TGT CCA    718
 D   S   T   C   C   E   L   P   T   G   K   Y   G   C   C   P    232

ATG CCC AAT GCC ATC TGC TGT TCC GAC CAC CTG CAC TGC TGC CCC CAG    766
 M   P   N   A   I   C   C   S   D   H   L   H   C   C   P   Q    248

GAC ACT GTA TGT GAC CTG ATC CAG AGT AAG TGC CTA TCC AAG AAC TAC    814
 D   T   V   C   D   L   I   Q   S   K   C   L   S   K   N   Y    264

ACC ACG GAT CTC CTG ACC AAG CTG CCT GGA TAC CCA GTG AAG GAG GTG    862
 T   T   D   L   L   T   K   L   P   G   Y   P   V   K   E   V    280

AAG TGC GAC ATG GAG GTG AGC TGC CCT GAA GGA TAT ACC TGC TGC CGC    910
 K   C   D   M   E   V   S   C   P   E   G   Y   T   C   C   R    296

CTC AAC ACT GGG GCC TGG GGC TGC TGT CCA TTT GCC AAG GCC GTG TGT    958
 L   N   T   G   A   W   G   C   C   P   F   A   K   A   V   C    312

TGT GAG GAT CAC ATT CAT TGC TGC CCG GCA GGG TTT CAG TGT CAC ACA   1006
 C   E   D   H   I   H   C   C   P   A   G   F   Q   C   H   T    328

GAG AAA GGA ACC TGC GAA ATG GGT ATC CTC CAA GTA CCC TGG ATG AAG   1054
 E   K   G   T   C   E   X   G   I   L   Q   V   P   W   M   K    344

AAG GTC ATA GCC CCC CTC CGC CTG CCA GAC CCA CAG ATC TTG AAG AGT   1102
 K   V   I   A   P   L   R   L   P   D   P   Q   I   L   K   S    360

GAT ACA CCT TGT GAT GAC TTC ACT AGG TGT CCT ACA AAC AAT ACC TGC   1150
 D   T   P   C   D   D   F   T   R   C   P   T   N   N   T   C    376

TGC AAA CTC AAT TCT GGG GAC TGG GGC TGC TGT CCC ATC CCA GAG GCT   1198
 C   K   L   N   S   G   D   W   G   C   C   P   I   P   E   A    392

GTC TGC TGC TCA GAC AAC CAG CAT TGC TGC CCT CAG GGC TTC ACA TGT   1246
 V   C   C   S   D   N   Q   H   C   C   P   Q   G   F   T   C    408

CTG GCT CAG GGG TAC TGT CAG AAG GGA GAC ACA ATG GTG GCT GGC CTG   1294
 L   A   Q   G   Y   C   Q   K   G   D   T   M   V   A   G   L    424

GAG AAG ATA CCT GCC CGC CAG ACA ACC CCG CTC CAA ATT GGA GAT ATC   1342
 E   K   I   P   A   R   Q   T   T   P   L   Q   I   G   D   I    440
```

FIG.8B

Mouse GP88 cDNA (continued)

```
GGT TGT GAC CAG CAT ACC AGC TGC CCA GTA GGG CAA ACC TGC TGC CCA   1390
 G   C   D   Q   H   T   S   C   P   V   G   Q   T   C   C   P    456

AGC CTC AAG GGA AGT TGG GCC TGC TGC CAG CTG CCC CAT GCT GTG TGC   1438
 S   L   K   G   S   W   A   C   C   Q   L   P   H   A   V   C    472

TGT GAG GAC CGG CAG CAC TGT TGC CCG GCC GGG TAC ACC TGC AAC GTG   1486
 C   E   D   R   Q   H   C   C   P   A   G   Y   T   C   N   V    488

AAG GCG AGG ACC TGT GAG AAG GAT GTC GAT TTT ATC CAG CCT CCC GTG   1534
 K   A   R   T   C   E   K   D   V   D   F   I   Q   P   P   V    504

CTC CTG ACC CTC GGC CCT AAG GTT GGG AAT GTG GAG TGT GGA GAA GGG   1582
 L   L   T   L   G   P   K   V   G   N   V   E   C   G   E   G    520

CAT TTC TGC CAT GAT AAC CAG ACC TGT TGT AAA GAC AGT GCA GGA GTC   1630
 H   F   C   H   D   N   Q   T   C   C   K   D   S   A   G   V    536

TGG GCC TGC TGT CCC TAC CTA AAG GGT GTC TGT TGT AGA GAT GGA CGT   1678
 W   A   C   C   P   Y   L   K   G   V   C   C   R   D   G   R    552

CAC TGT TGC CCC GGT GGC TTC CAC TGT TCA GCC AGG GGA ACC AAG TGT   1726
 H   C   C   P   G   G   F   H   C   S   A   R   G   T   K   C    568

TTG CGA AAG AAG ATT CCT CGC TGG GAC ATG TTT TTG AGG GAT CCG GTC   1774
 L   R   K   K   I   P   R   W   D   M   F   L   R   D   P   V    584

CCA ACA CCG CTA CTG TAA GGA AGG GCT ACA GAC TTA AGG AAC TCC ACA   1822
 P   T   P   L   L   *                                            589

GTC CTG GGA ACC TGT TTC GAG GGT TAC CCA CTA CTC AGG CCT CCC TAG   1870
CGC CTC CTC CCC TAA CGT CTC CCC GGC CTA CTC ATC CTG AGT CAC CCT   1918
ATC ACC ATG GGA GGT GGA GCC TCA AAC TAA AAC CTT CTT TTA TGG AAA   1966
GAA GGC TGT GGC CAA AAG CCC CGT ATC AAA CTG CCA TTT CTT CCG GTT   2014
TCT GTG GAC CTT GTG GCC AGG TGC TCT TCC CGA GCC ACA GGT GTT CTG   2062
TGA GCT TGC TTG TGT GTG TGT GCG CGT GTG CGT GTG TTG CTC AAA TAA   2110
AGT TTG TAC GCT TTC TGA AAA AAA AAA                               2137
```

FIG.8C

Nucleotide sequence of human granulin/epithelin precursor (human GP88).
Human Granulin Genbank M75161$

```
cgcaggcaga ccatgtggac cttggtgagc tgggtggcct taacagcagg gctggtggct
ggaacgcggt gcccagatgg tcagttctgc cctgtggcct gctgcctgga ccccggagga
gccagctaca gctgctgccg tccccttctg gacaaatggc ccacaacact gagcaggcat
ctgggtggcc cctgccaggt tgatgcccac tgctctgccg gccactcctg catctttacc
gtctcaggga cttccagttg ctgccccttc ccagaggccg tggcatgcgg ggatggccat
cactgctgcc cacggggctt ccactgcagt gcagacggga gatcctgctt ccaaagatca
ggtaacaact ccgtgggtgc catccagtgc cctgatagtc agttcgaatg cccggacttc
tccacgtgct gtgttatggt cgatggctcc tgggggtgct gccccatgcc ccaggcttcc
tgctgtgaag acagggtgca ctgctgtccg cacggtgcct ctgcgacct ggttcacacc
cgctgcatca cacccacggg cacccacccc ctggcaaaga agctccctgc cagaggact
aacagggcag tggccttgtc cagctcggtc atgtgtccgg acgcacggtc ccggtgccct
gatggttcta cctgctgtga gctgcccagt gggaagtatg gctgctgccc aatgcccaac
gccacctgct gctccgatca cctgcactgc tgcccccaag acactgtgtg tgacctgatc
cagagtaagt gcctctccaa ggagaacgct accacggacc tcctcactaa gctgcctgcg
cacacagtgg gcgatgtgaa atgtgacatg gaggtgagct gcccagatgg ctataccgtc
tgccgtctac agtcgggggc ctgggctgc tgccttta cccaggctgt gtgctgtgag
gaccacatac actgctgtcc cgcggggttt acgtgtgaca cgcagaaggg tacctgtgaa
caggggcccc accaggtgcc ctggatggag aaggccccag ctcacctcag cctgccagac
ccacaagcct tgaagagaga tgtccctgt gataatgtca gcagctgtcc ctcctccgat
acctgctgcc aactcacgtc tggggagtgg ggctgctgtc caatcccaga ggctgtctgc
tgctcggacc accagcactg ctgcccccag cgatacacgt gtgtagctga ggggcagtgt
cagcgaggaa gcgagatcgt ggctggactg gagaagatgc ctgcccgccg cggttcctta
tcccaccca gagacatcgg ctgtgaccag cacaccagct gcccggtggg cggaacctgc
tgcccgagcc agggtgggag ctgggcctgc tgccagttgc cccatgctgt gtgctgcgag
gatcgccagc actgctgccc ggctggctac acctgcaacg tgaaggctcg atcctgcgag
aaggaagtgg tctctgccca gcctgccacc ttcctggccc gtagccctca cgtgggtgtg
aaggacgtgg agtgtgggga aggacacttc tgccatgata accagacctg ctgccgagac
aaccgacagg gctgggcctg ctgtccctac gcccagggcg tctgttgtgc tgatcggcgc
cactgctgtc ctgctggctt ccgctgcgca cgcaggggta ccaagtgttt gcgcagggag
gccccgcgct gggacgcccc tttgagggac ccagccttga cagctgct gtgagggaca
gtactgaaga ctctgcagcc ctcgggaccc cactcggagg gtgccctctg ctcaggcctc
gtactgaaga ctctgcagcc ctcgggaccc cactcggagg gtgccctctg ctcaggcctc
cctagcacct cccctaacc aaattctccc tggacccat tctgagctcc ccatcaccat
gggaggtggg gcctcaatct aaggcccttc cctgtcagaa gggggttgag gcaaaagccc
attacaagct gccatcccct ccccgtttca gtggaccctg tggccaggtg cttttcccta
tccacagggg tgtttgtgtg ttgggtgtgc tttcaataaa gtttgtcact ttctt*
```

FIG.9A

Amino-acid sequence of human granulin/epithelin precursor (human GP88).

MWTLVSWVALTAGLVAGTRCPDGQFCPVACCLDPGGASYSCCRP
LLDKWPTTLSRHLGGPCQVDAHCSAGHSCIFTVSGTSSCCPFPEAVACGDGHHCCPRG
FHCSADGRSCFQRSGNNSVGAIQCPDSQFECPDFSTCCVMVDGSWGCCPMPQASCCED
RVHCCPHGAFCDLVHTRCITPTGTHPLAKKLPAQRTNRAVALSSSVMCPDARSRCPDG
STCCELPSGKYGCCPMPNATCCSDHLHCCPQDTVCDLIQSKCLSKENATTDLLTYLPA
HTVGDVKCDMEVSCPDGYTCCRLQSGAWGCCPFTQAVCCEDHIHCCPAGFTCDTQKGT
CEQGPHQVPW<u>MEKAPAHLSLPDPQALKRDV</u>PCDNVSSCPSSDTCCQLTSGEWGCCPIP
EAVCCSDHQHCCPQRYTCVAEGQCQRGSEIVAGLEKMPARRGSLSHPRDIGCDQHTSC
PVGGTCCPSQGGSWACCQLPHAVCCEDRQHCCPAGYTCNVKARSCEKEVVSAQPATFL
ARSPHVGVKDVECGEGHFCHDNQTCCRDNRQGWACCPYAQGVCCADRRHCCPAGFRC<u>A
RRGTKCLRREAPR</u>WDAPLRDPALRQLL*

FIG.9B

MOUSE GP88 PROTEIN SEQUENCE
MNVLMSWLAFAAGLVAG 17

TQCPDGQF-CPVA--CCLDQC-GANYSCCNPLLDTWPRITSHHL  57

DGSC-QTHGHCPAGY-SCLLTVSGTS-SCCPFSKGVSCGDGYHCCPQGFHCSADGKSCFQMSDNPL  120

GAVQCPGSQFECPDSATCCIMVD-G-SWGCCPMPQASCCEDRVHCCPHGASCDLVHTRCVSPTGTHTLLKKFPAQKTNRRVSLPFS  204    g

VVCPDAKTQCPDDSTCCELP-TGK-YGCCPMPNAICCSDHLHCCPQDTVCDLIQSKCLSKNYTTDLLTKLPGYPVK  278    f

EVKC-DMEVSCPEGYTCCRLN-TGA-WGCCPFAKAVCCEDHIHCCPAGFQCHTEKGICEMGILQVPWMKKVIAPRRLPDPQILKS  360    2,B

DIPCDDFTR-CPTNNTCCKLN-SGD-WGCCPIPEAVCCSDNQHCCPQGFTCLAQGY-CQKGDTMVAGLEKIPARQTTPLQIG  438    1,A

DIGCDWHL-SCPVGQTCCPSLK-G-SWACCQLPHAVCCEDRQHCCPAGYTCNVKARTCEKDVDFIQPPVLLTLGPKVG  513    C

NVECGEGHF-CHDNQTCCKDSA-GV-WACCPYLKGVCCRDGRHCCPGGFHCSARGTKCLRKKIPRWDMFLRDPVPRPLL  589    D
                                                                                      e consensus sequence:
C.....C.....CC......G....CC......CC.D.HCCP....C......C 1,2: MOUSE EPITHELIN 1,2.
A,B,C,D,e,f,g: granulin A,B,C,D,E,F,G: N-terminus of granulin A,B,C,D have been sequenced.
Mouse epithelin precursor sequence is from Plowman et al (1992)

FIG. 10

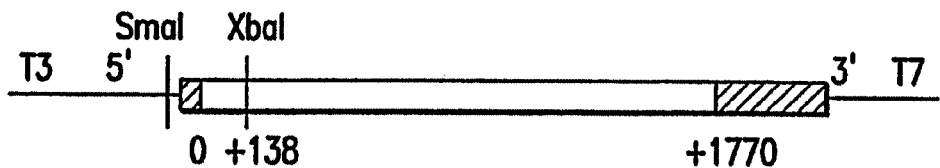
GP88 cDNA CLONE in SK
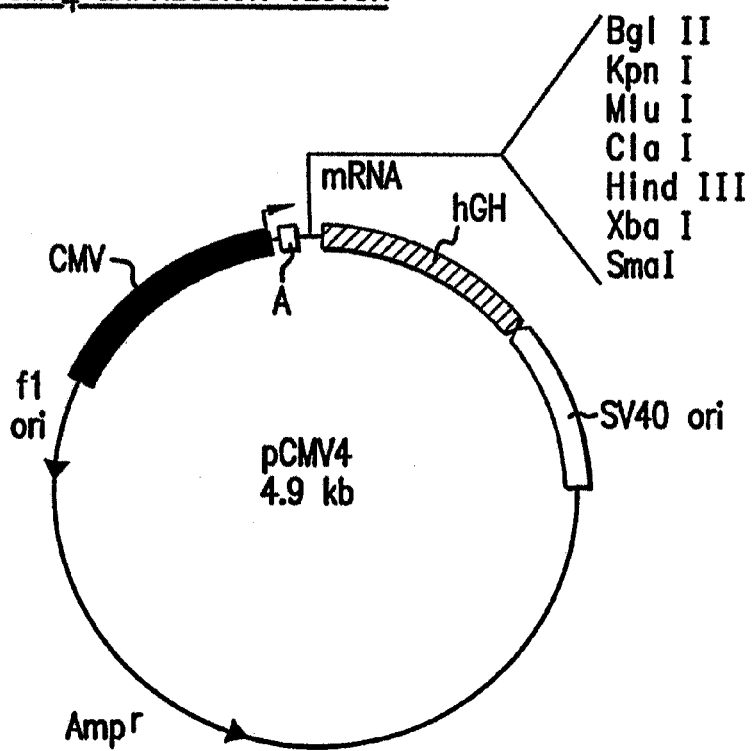
STRUCTURE OF pCMV4 EXPRESSION VECTOR
FIG.11

GP88 EXPRESSION IN NON TUMORIGENIC (MCF 10A) AND MALIGNANT (MCF 7, MDA-468) HUMAN MAMMARY EPITHELIAL CELLS

GP88 EXPRESSION IS INHIBITED BY ANTISENSE GP88 cDNA TRANSFECTION IN HUMAN BREAST CARCINOMA MDA-468

PCDGF  + +
PD98059 - +

PCDGF    -    +    +
LY294002 -    -    +

Con   IL-6   PCDGF

METHODS AND COMPOSITIONS FOR INHIBITING THE GROWTH OF HEMATOPOIETIC MALIGNANT CELLS

This application is a continuation of application Ser. No. 10/321,587, filed Dec. 18, 2002, now abandoned, which is a continuation-in-part of U.S. application Ser. No. 09/456,886, filed Dec. 8, 1999, now U.S. Pat. No. 6,720,159, which is a divisional of U.S. application Ser. No. 08/991,862, filed Dec. 16, 1997, now U.S. Pat. No. 6,309,826, which is a continuation-in-part of U.S. patent application Ser. No. 08/863,079, filed May 23, 1997, now abandoned all of which are hereby incorporated by reference in their entirety.

FIELD OF THE INVENTION

This invention relates to cell biology, physiology and medicine, and concerns an 88 kDa glycoprotein growth factor ("GP88" or "PCDGF") and compositions and methods which affect the expression and biological activity of GP88. These compositions and methods are useful for diagnosis and treatment of diseases including cancer.

REFERENCES

Several publications are referenced herein by Arabic numerals within parenthesis. Full citations for these references may be found at the end of the specification immediately preceding the claims.

BACKGROUND OF THE INVENTION

The proliferation and differentiation of cells in multicellular organisms is subject to a highly regulated process. A distinguishing feature of cancer cells is the absence of control over this process; proliferation and differentiation become deregulated resulting in uncontrolled growth. Significant research efforts have been directed toward better understanding this difference between normal and tumor cells. One area of research focus is growth factors and, more specifically, autocrine growth stimulation.

Growth factors are polypeptides which carry messages to cells concerning growth, differentiation, migration and gene expression. Typically, growth factors are produced in one cell and act on another cell to stimulate proliferation. However, certain malignant cells, in culture, demonstrate a greater or absolute reliance on an autocrine growth mechanism. Malignant cells which observe this autocrine behavior circumvent the regulation of growth factor production by other cells and are therefore unregulated in their growth.

Study of autocrine growth control advances understanding of cell growth mechanisms and leads to important advances in the diagnosis and treatment of cancer. Toward this end, a number of growth factors have been studied, including insulin-like growth factors ("IGF-I" and "IGF-II"), gastrin-releasing peptide ("GRP"), transforming growth factors alpha and beta ("TGF-a" and "TGF-b"), and epidermal growth factor ("EGF").

The present invention is directed to a recently discovered growth factor. This growth factor was first discovered in the culture medium of a highly tumorigenic "PC cell line," an insulin-independent variant isolated from the teratoma derived adipogenic cell line 1246. This growth factor is referred to herein as "GP88." GP88 has been purified and structurally characterized. Amino acid sequencing of GP88 indicates that GP88 has amino acid sequence similarities with the mouse granulin/epithelin precursor.

Granulins/epithelins ("grn/epi") are 6 kDa polypeptides and belong to a novel family of double cysteine rich polypeptides. U.S. Pat. No. 5,416,192 (Shoyab et al.) is directed to 6 kDa epithelins, particularly epithelin 1 and epithelin 2. According to Shoyab, both epithelins are encoded by a common 63.5 kDa precursor, which is processed into smaller forms as soon as it is synthesized, so that the only natural products found in biological samples are the 6 kDa forms. Shoyab et al. teaches that the epithelin precursor is biologically inactive.

Contrary to the teachings of Shoyab et al., the inventor's laboratory has demonstrated that the precursor is not processed as soon as it is synthesized. Studies, conducted in part by this inventor, have demonstrated that the precursor (i.e., GP88) is in fact secreted as an 88 kDa glycoprotein with an N-linked carbohydrate moiety of 20 kDa. Analysis of the N-terminal sequence of GP88 indicates that GP88 starts at amino acid 17 of the grn/epi precursor, demonstrating that the first 17 amino acids from the protein sequence deduced from the precursor cDNA correspond to a signal peptide compatible with targeting for membrane localization or for secretion.

Also in contrast to the teachings of Shoyab et al., the inventor demonstrated that GP88 is biologically active and has growth promoting activity, particularly as an autocrine growth factor for the producer cells.

Hematopoietic malignancies are malignant blood diseases including various lymphomas and leukemias. Leukemias of B-cell lineage include, but are not limited to, acute lymphocytic leukemia, B cell lymphoma, and multiple myeloma. Multiple myeloma ("MM") is a clonal B-cell neoplasm and the second most prevalent blood cancer, representing 1% of all cancers and 2% of all cancer deaths. B-cells (or B-lymphocytes) are precursor cells that differentiate into plasma cells after exposure to particular antigens. Plasma cells produce immunoglobulins and have a limited life span. However, uncontrolled growth of plasma cells in a clonal lineage of B cells may lead to accumulation of plasma cells producing monoclonal immunoglobulins or immunoglobulin fragments (e.g., M protein). MM is characterized by bone degradation and fractures, anemia, increased risk of infection, and decreased production of platelets in addition to other symptoms. The incidence of MM, currently about 14,000 new cases per year, has been steadily increasing in the United States for several decades (1). There has been little improvement in the treatment of human MM over the past 25 years and there is no cure for the disease (3). The few available therapies for treatment of MM have severe side effects and are of limited efficacy. For nearly 3 decades, the standard treatment for human MM has been glucocorticoid and/or chemotherapy with melphalan and prednisone alone or combinations of alkylating agents such as glucocorticoids and anthracyclines (4). However, almost all patients with MM who initially respond to glucocorticoid therapy relapse, with a median survival of two to three years following diagnosis (5). During the progression of MM to more aggressive forms of the disease, MM cells become insensitive to the killing effect of glucocorticoids leaving only the use of chemotherapeutic agents to control the disease.

What is needed are new compositions and methods for treatment and diagnosis of MM, and particularly compositions and methods that inhibit the proliferation and survival of multiple myeloma cells.

SUMMARY OF INVENTION

The inventor has now unexpectedly discovered that a glycoprotein (GP88), which is expressed in a tightly regulated fashion in normal cells, is overexpressed and unregulated in highly tumorigenic cells derived from the normal cells, that GP88 acts as a stringently required growth stimulator and survival factor for the tumorigenic cells and that inhibition of GP88 expression or action in the tumorigenic cells results in an inhibition of the tumorigenic properties of the overproducing cells.

The inventor has further discovered that GP88 is overexpressed in hematopoietic malignant cells such as leukemia cells of B-cell lineage (e.g., acute lymphocytic leukemia, B cell lymphoma, and multiple myeloma). GP88 stimulates the tumorigenic properties of hematopoietic malignant cells while inhibition of GP88 expression and biological activity greatly reduces the tumorigenic properties of hematopoietic malignant cells. An embodiment of the invention provides methods of inhibiting the growth or viability of hematopoietic malignant cells. In one embodiment of the invention, a GP88 antagonist inhibits multiple myeloma cell growth. In another embodiment of the invention, a composition for inhibiting the growth or viability of hematopoietic malignant cells comprising a GP88 antagonist (e.g., an anti-GP88 antibody, or anti-GP88 nucleic acid) is provided. In yet another embodiment, a method of diagnosing B-cell leukemia is provided comprising detecting GP88 (e.g., GP88 protein, or nucleic acids encoding GP88) in a tissue sample containing B cells (e.g., tissue suspected of containing myeloma cells including, but not limited to blood, bone marrow, lymph, liver, and spleen) and diagnosing multiple myeloma by determining whether GP88 protein is present in the tissue sample. The presence of GP88 in B cells indicates multiple myeloma. Alternatively, detecting GP88 in B-cells indicates the presence of leukemia cells of B-cell lineage. Thus, the presence of GP88 serves as a prognostic marker for B-cell leukemia.

The invention also provides methods for determining whether a patient is responding or responsive to glucocorticoid therapy by comparing the level of GP88 in a tissue sample containing B-cells at a first time with the level of GP88 in a tissue sample containing B-cells at a second time. Increased levels of GP88 in tissue samples over time indicate a patient is not responding or responsive to glucocorticoid therapy.

This invention provides GP88 antagonizing compositions capable of inhibiting the expression or activity of GP88, methods for treating diseases associated with a defect in GP88 quantity or activity such as but not limited to cancer in a mammal in tissues including, for example, blood, cerebrospinal fluid, serum, plasma, urine, nipple aspirate, liver, kidney, breast, bone, bone marrow, testes, brain, ovary, skin, and lung, methods for determining the susceptibility of a subject to diseases associated with a defect in GP88 expression or action, methods for measuring susceptibility to GP88 antagonizing therapy, and methods, reagents, and kits for the in vitro and in vivo detection of GP88 and tumorigenic activity in cells.

Additional objects and advantages of the invention will be set forth in part in the description that follows, and in part will be obvious from the description, or may be learned by the practice of the invention.

To achieve the objects and in accordance with the purpose of the invention, as embodied and properly described herein, the present invention provides compositions for diagnosis and treatment of diseases such as but not limited to multiple myeloma in which cells exhibit an altered expression of GP88 or altered response to GP88.

Use of the term "altered expression" herein means increased expression or overexpression of GP88 by a statistically significant amount as compared to corresponding normal cells or surrounding peripheral cells. The term "altered expression" also means expression which became unregulated or constitutive without being necessarily elevated. Use of the terms increased or altered "response" to GP88 means a condition wherein increase in any of the biological functions (e.g., growth, differentiation, viral infectivity) conferred by GP88 results in the same or equivalent condition as altered expression of GP88.

Use of the term "GP88" herein means epithelin/granulin precursor in cell extracts and extracellular fluids, and is intended to include not only GP88 according to the amino acid sequences included in FIG. 8 or 9, which are of mouse and human origins, but also GP88 of other species. "GP88" does not include epithelin 1 or epithelin 2 peptides as described in U.S. Pat. No. 5,416,192 (Shoyab et al.). In addition, the term also includes functional derivatives thereof having additional components such as a carbohydrate moiety including a glycoprotein or other modified structures.

Also intended by the term GP88 is any polypeptide fragment having at least 10 amino acids present in the above mentioned sequences. Sequences of this length are useful as antigens and for making immunogenic conjugates with carriers for the production of antibodies specific for various epitopes of the entire protein. Such polypeptides are useful in screening such antibodies and in the methods directed to detection of GP88 in biological fluids. It is well known in the art that peptides are useful in generation of antibodies to larger proteins (7). In one embodiment of this invention, it is shown that peptides from 12-19 amino-acids in length have been successfully used to develop antibodies that recognize full length GP88.

The polypeptide of this invention may exist covalently or non-covalently bound to another molecule. For example, it may be fused to one or more other polypeptides via one or more peptide bonds such as glutathione transferase, polyhistidine, or myc tag.

The polypeptide is sufficiently large to comprise an antigenetically distinct determinant or epitope which can be used as an immunogen to reproduce or test antibodies against GP88 or a functional derivative thereof.

One embodiment includes the polypeptide substantially free of other mammalian peptides. GP88 of the present invention can be biochemically or immunochemically purified from cells, tissues or a biological fluid. Alternatively, the polypeptide can be produced by recombinant means in a prokaryotic or eukaryotic expression system and host cells.

"Substantially free of other mammalian polypeptides" reflects the fact that the polypeptide can be synthesized in a prokaryotic or a non-mammalian or mammalian eukaryotic organism, if desired. Alternatively, methods are well known for the synthesis of polypeptides of desired sequences by chemical synthesis on solid phase supports and their subsequent separation from the support. Alternatively, the protein can be purified from tissues or fluids of mammals where it naturally occurs so that it is at least 90% pure (on a weight basis) or even 99% pure, if desired, of other mammalian polypeptides, and is therefore substantially free from them. This can be achieved by subjecting the tissue extracts or fluids to standard protein purification such as on immunoabsorbants bearing antibodies reactive against the protein. One embodiment of the present invention describes purification methods for the purification of naturally occurring GP88 and of recombinant GP88 expressed in baculovirus infected insect cells. Alternatively, purification from such tissues or fluids can be achieved by a combination of standard methods such as but not limited to the ones described in reference (4).

As an alternative to a native purified or recombinant glycoprotein or polypeptide, "GP88" is intended to also include functional derivatives. By functional derivative is meant a "fragment," "variant," "analog," or "chemical derivative" of the protein or glycoprotein as defined below. A functional derivative retains at least a portion of the function of the full length GP88 which permits its utility in accordance with the present invention.

A "fragment" of GP88 refers to any subset of the molecule that is a shorter peptide that retains the tumorigenic properties of the full-length GP88 protein. This corresponds for example but is not limited to regions such as K19T and S14R for mouse GP88, and E19V and A14R (equivalent to murine K19T and S14R, respectively) for human GP88.

A "variant" of GP88 refers to a molecule substantially similar to either the entire peptide or a fragment thereof. Variant peptides may be prepared by direct chemical synthesis of the variant peptide using methods known in the art.

Alternatively, amino acid sequence variants of the peptide can be prepared by modifying the DNA which encodes the synthesized protein or peptide. Such variants include, for example, deletions, insertions, or substitutions of residues within the amino-acid sequence of GP88. Any combination of deletion, insertion, and substitution may also be made to arrive at the final construct, provided the final construct possesses the desired activity. The mutation that will be made in the DNA encoding the variant peptide must not alter the reading frame and preferably will not create complementary regions that could produce secondary mRNA structures. At the genetic level these variants are prepared by site directed mutagenesis (8) of nucleotides in the DNA encoding the peptide molecule thereby producing DNA encoding the variant, and thereafter expressing the DNA in recombinant cell culture. The variant typically exhibits the same qualitative biological activity as the nonvariant peptide.

An "analog" of GP88 protein refers to a non-natural molecule substantially similar to either the entire molecule or a fragment thereof.

A "chemical derivative" contains additional chemical moieties not normally a part of the peptide or protein. Covalent modifications of the peptide are also included within the scope of this invention. Such modifications may be introduced into the molecule by reacting targeted amino-acid residues of the peptide with an organic derivatizing agent that is capable of reacting with selected side chains or terminal amino-acid residues. Most commonly derivatized residues are cysteinyl, histidyl, lysinyl, arginyl, tyrosyl, glutaminyl, asparaginyl and amino terminal residues. Hydroxylation of proline and lysine, phosphorylation of hydroxyl groups of seryl and threonyl residues, methylation of the alpha-amino groups of lysine, histidine, and histidine side chains, acetylation of the N-terminal amine and amidation of the C-terminal carboxylic groups. Such derivatized moieties may improve the solubility, absorption, biological half life and the like. The moieties may also eliminate or attenuate any undesirable side effect of the protein and the like. In addition, derivatization with bifunctional agents is useful for cross-linking the peptide to water insoluble support matrices or to other macromolecular carriers. Commonly used cross-linking agents include glutaraldehyde, N-hydroxysuccimmide esters, homobifunctional imidoesters, 1,1-bis(-diazoloacetyl)-2-phenylethane, and bifunctional maleimides. Derivatizing agents such as methyl-3-[9p-azidophenyl)]dithiopropioimidate yield photoactivatable intermediates that are capable of forming crosslinks in the presence of light. Alternatively, reactive water-insoluble matrices such as cyanogen bromide activated carbohydrates and the reactive substrates described in U.S. Pat. Nos. 3,969,287 and 3,691,016 may be employed for protein immobilization.

Use of the term GP88 "antagonizing agents" herein means any composition that inhibits or blocks GP88 expression, production or secretion, or any composition that inhibits or blocks the biological activity of GP88. This can be achieved by any mode of action such as but not limited to the following:

(A) GP88 antagonizing agents include any reagent or molecule inhibiting GP88 expression or production including but not limited to:

(1) antisense GP88 DNA or RNA molecules that inhibit GP88 expression by inhibiting GP88 translation;

(2) reagents (hormones, growth factors, small molecules) that inhibit GP88 mRNA and/or protein expression at the transcriptional, translational or post-translational levels;

(3) factors, reagents or hormones that inhibit GP88 secretion;

(B) GP88 antagonizing agents also include any reagent or molecule that will inhibit GP88 action or biological activity such as but not limited to:

(1) neutralizing antibodies to GP88 that bind the protein and prevent it from exerting its biological activity;

(2) antibodies to the GP88 receptor that prevent GP88 from binding to its receptor and from exerting its biological activity;

(3) competitive inhibitors of GP88 binding to its receptors (e.g., proteins, ribozymes, aptamers, small molecules);

(4) inhibitors of GP88 signaling pathways (e.g., proteins, ribozymes, aptamers, small molecules).

Specific examples presented herein provide a description of preferred embodiments, particularly the use of neutralizing antibodies to inhibit GP88 biological action and the growth of multiple myeloma cells; the use of antisense GP88 cDNA and antisense GP88 oligonucleotides to inhibit GP88 expression leading to inhibition of the tumorigenic properties of PC cells; characterization of GP88 receptors on cell surfaces of several cell lines including the mammary epithelial cell line C57MG, the 1246 and PC cell lines and the mink lung epithelial cell line CCL64.

In one embodiment of the invention, the GP88 antagonizing agents are antisense oligonucleotides to GP88. The antisense oligonucleotides preferably inhibit GP88 expression by inhibiting translation of the GP88 protein. In another embodiment, the antagonizing agent is RNAi (RNA interference nucleic acids). RNAi are double-stranded RNA molecules that are homologous to the target gene (e.g., GP88) and interfere with the target gene's activity.

Alternatively, such a composition may comprise reagents, factors or hormones that inhibit GP88 expression by regulating GP88 gene transcriptional activity. Such a composition may comprise reagents, factors or hormones that inhibit GP88 post-translational modification and its secretion. Such a composition may comprise reagents that act as GP88 antagonists that block GP88 activity by competing with GP88 for binding to GP88 cell surface receptors. Alternatively, such a composition may comprise factors or reagents that inhibit the signaling pathway transduced by GP88 once binding to its receptors on diseased cells.

The composition may also comprise reagents that block GP88 action such as an antibody specific to GP88 that neutralizes its biological activity, or an antibody to the GP88 receptor that blocks its activity.

The antibodies of the invention (neutralizing and others) are preferably used as a treatment for multiple myeloma or other diseases in cells which exhibit an increased expression of GP88. By the term "neutralizing" it shall be understood that the antibody has the ability to inhibit or block the normal biological activity of GP88, including GP88's ability to stimulate cell proliferation, increase cell survival, or to induce tumor growth in experimental animals and in humans. An effective amount of anti-GP88 antibody is administered to an animal, including humans, by various routes. In an alternative embodiment, the anti-GP88 antibody is used as a diagnostic to detect cells which exhibit an altered (increased) expression of GP88 as occurring in diseases such as but not limited to cancers (e.g., multiple myeloma), and to identify diseased cells whose growth is dependent on GP88 and which will respond to GP88 antagonizing therapy. In yet another embodiment, the anti-GP88 antibody is used to deliver compounds such as cytotoxic factors or antisense oligonucleotides to cells expressing or responsive to GP88. The cytotoxic factors may be attached, linked, or associated with the anti-GP88 antibody.

The antisense oligonucleotides of the invention are also used as a treatment for cancer in cells which exhibit an increased expression of GP88, such as hematopoietic malignant cells (e.g., B-cell leukemia cells). An effective amount of the antisense oligonucleotide is administered to an animal, including humans, by various routes.

The present invention also provides a method for determining the susceptibility to diseases associated with a defect in GP88 expression or action which comprises obtaining a sample of biological fluid or tissue and measuring the amount of GP88 in the fluid or tissue or measuring the susceptibility of the cells to respond to GP88. In the case of cancer (e.g., hematopoietic malignancy), the amount of GP88 being proportional to the susceptibility to the cancer.

The present invention also provides a method for measuring the degree of severity of cancer (e.g., hematopoietic malignancy) which comprises obtaining a sample of biological fluid or tissue and measuring the amount of GP88 in the fluid or tissue sample, the amount of GP88 being proportional to the degree or severity of the cancer. In one embodiment of the invention, the tissue sample is derived from bone, bone marrow, or serum. In another embodiment of the invention, the presence of GP88 in B cells is detected.

The present invention also provides a method for measuring susceptibility to GP88 antagonizing therapy which comprises obtaining a sample of the diseased tissue (biopsy) or a tissue suspected of being diseased, maintaining the cells derived from the sample in culture, treating the cells derived from the culture with anti-GP88 neutralizing antibody and determining if the neutralizing antibody inhibits the cell growth. The ability of the antibody to inhibit cell growth is indicative that the cells are dependent on GP88 to proliferate and is predictive that GP88 antagonizing therapy will be efficacious. In addition, the invention provides methods for determining whether a patient is responding or responsive to glucocorticoid therapy by comparing the level of GP88 in a tissue sample taken at a first time with a tissue sample taken at a second time. Increased levels of GP88 in tissue samples containing B-cells indicates the patient is not responding or is not responsive to glucocorticoid therapy.

The present invention also provides a method for determining the susceptibility to cancer associated with an abnormality in GP88 receptor level or activity which comprises obtaining a sample of tissue and measuring the amount of GP88 receptor protein or mRNA in the tissue or measuring the kinase activity of the receptor in the tissue (GP88 binding to its receptor induces phosphorylation of cellular proteins including the receptor for GP88).

The present invention also provides a method for targeting GP88 antagonizing reagents to the diseased site by conjugating them to an anti-GP88 antibody or an anti-GP88 receptor antibody.

The accompanying drawings, which are incorporated in and constitute a part of this specification, illustrate embodiments of the invention and, together with the description, serve to explain the principles of the invention.

BRIEF DESCRIPTION OF THE DRAWINGS

FIG. 5 shows GP88 mRNA expression levels in estrogen receptor positive and estrogen receptor negative human mammary carcinoma cell lines.

FIG. 8 shows the nucleotide and deduced amino-acid sequence of mouse GP88 (SEQ ID NO:1). Peptide regions used as antigens to raise anti-GP88 antibodies K19T and S14R are underlined. The region cloned in the antisense orientation in the pCMV4 mammalian expression vector is indicated between brackets.

FIG. 9A shows the nucleotide sequence of human GP88 cDNA (SEQ ID NO:16). Indicated between brackets is the region cloned in the antisense orientation into the pcDNA3 mammalian expression system; and FIG. 9B shows the deduced amino-acid sequence of human GP88 (SEQ ID NO:17). The E19V region used as antigen to develop anti-human GP88 neutralizing antibody is underlined. It also indicates the region A14R equivalent to the mouse S14R region.

FIG. 10 shows the amino-acid sequence of mouse GP88 (SEQ ID NO:2) arranged to show the 7 and one-half repeats defined as granulins g, f, B, A, C, D and e (right side). This representation shows that the region K19T and S14R used to raise GP88 antibodies for developing anti-GP88 neutralizing antibodies is found between two epithelin/granulin repeats in what is considered a variant region. Indicated on the right hand side is the granulin classification of the repeats according to Bateman et al (6). Granulin B and granulin A are also defined as epithelin 2 and epithelin 1 respectively according to Plowman et al., 1992 (5).

FIG. 11 shows a schematic representation of pCMV4 and a GP88 cDNA clone indicating the restriction sites used to clone GP88 antisense cDNA into the expression vector.

FIG. 18A shows that GP88 increases the live cell density of serum starved RPMI 8226 cells while FIG. 18B shows that GP88 increases the percent viability of serum starved RPMI 8226.

FIG. 18A shows that GP88 increases the live cell density of serum starved ARP-1 cells while FIG. 18B shows that GP88 increases the percent viability of serum starved ARP-1 cells.

DETAILED DESCRIPTION OF THE INVENTION

Reference will now be made in detail to the presently preferred embodiments of the invention, which, together with the following examples, serve to explain the principles of the invention.

Biological Activity of GP88

The invention relates to GP88 and antitumor compositions useful for treating and diagnosing diseases linked to altered (increased) expression of GP88 (e.g., multiple myeloma). Alternatively this invention is used for treating and diagnosing diseases linked to increased responsiveness to GP88. Using a murine model system consisting of three cell lines, the inventor has shown that cells which overexpress GP88 form tumors. The parent cell line, 1246, is a C3H mouse adipogenic cell line which proliferates and differentiates into adipocytes in a defined medium under stringent regulation by insulin. The 1246 cells cannot form tumors in a syngeneic animal (C3H mouse) even when injected at a high cell density. An insulin independent cell line, 1246-3A, was isolated from 1246 cells maintained in insulin-free medium. The 1246-3A cells lost the ability to differentiate and form tumors when $10^6$ are injected subcutaneously in syngeneic mice. A highly tumorigenic cell line, PC, was developed from 1246-3A cells by an in vitro-in vivo shuttle technique. The PC cells formed tumors when $10^4$ cells were injected into syngeneic mice.

Figure 1A:
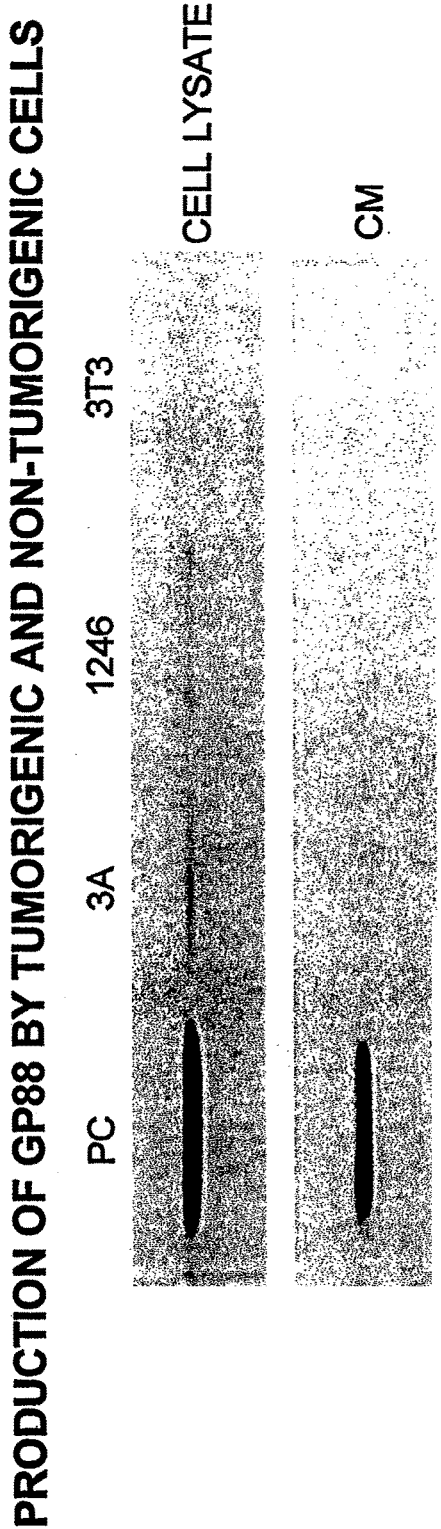
FIG. 1A compares the level of expression of GP88 protein in the 1246, 1246-3A and PC cell lines. Cells were cultured in DME-F12 medium supplemented with 2% fetal bovine serum (FBS). Immunoprecipitation and Western blot analysis with anti-K19T antibody measured GP88 expression levels.
Figure 1B:
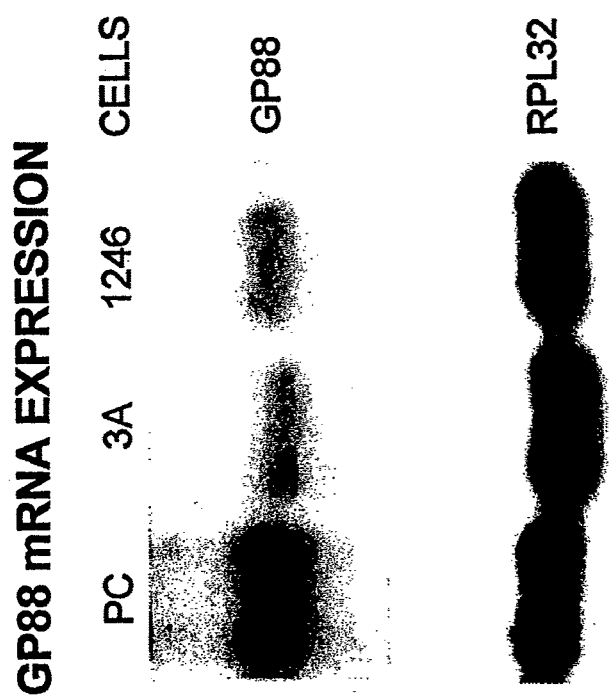
FIG. 1B compares the level of GP88 mRNA expression in the 1246, 1246-3A and PC cell lines. mRNA for RPL32 is used as an internal control for equal amounts of RNA loading.
Figure 1C:
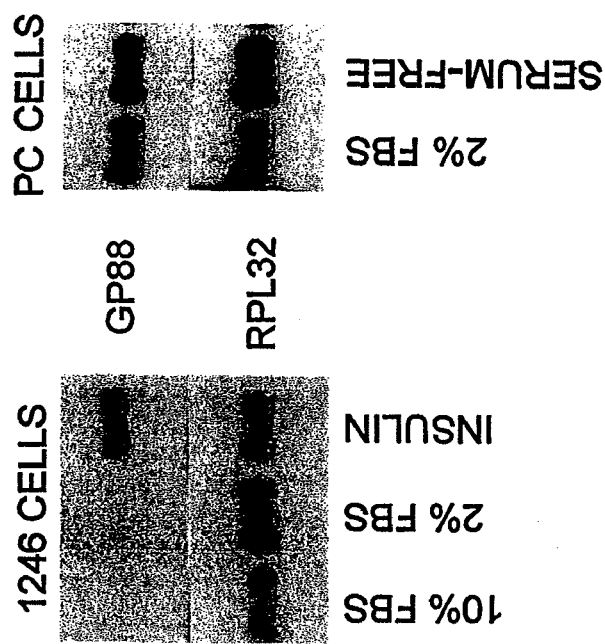
FIG. 1C compares the expression of GP88 mRNA in 1246 cells (left panel) and in PC cells (right panel) in serum-free and serum containing medium. The results show that GP88 expression in 1246 cells is inhibited by the addition of fetal bovine serum whereas such inhibition is not observed in the highly tumorigenic PC cells.

GP88 is overexpressed in the insulin-independent tumorigenic cell lines relative to the parent non-tumorigenic insulin-dependent cell line. Moreover, the degree of overexpression of GP88 positively correlates with the degree of tumorigenicity of these cells, demonstrating for the first time that GP88 is important in tumorigenesis (FIG. 1). With reference to FIG. 1, since GP88 is synthesized by cells but also secreted in culture medium, the level of GP88 was determined in cell lysates and in culture medium (CM). All cells were cultivated in DME/F12 nutrient medium supplemented with 2% fetal bovine serum. When cells reached confluency, culture medium (CM) was collected and cell lysates were prepared by incubation in buffer containing detergent followed by a 10,000×g centrifugation. Cell lysate and conditioned medium were normalized by cell number. Samples from cell lysate and conditioned medium were analyzed by Western blot analysis using an anti-GP88 antibody, as explained below.

Figure 2:
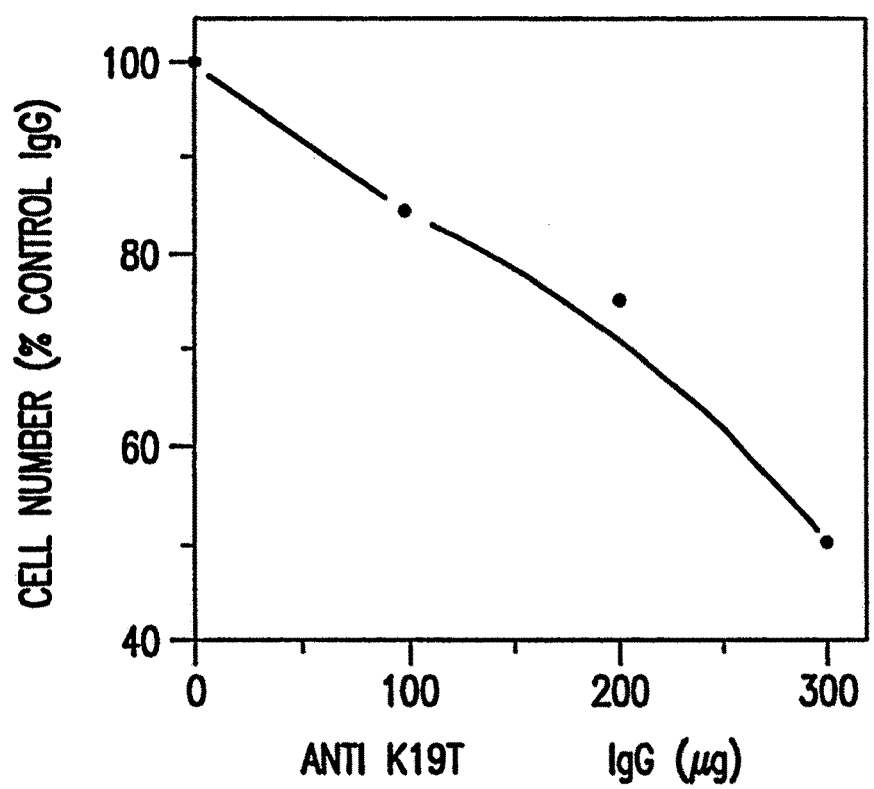
FIG. 2 illustrates the effect of treatment of the highly tumorigenic PC cells with increasing concentrations of anti-GP88 neutralizing antibody.

The development of a neutralizing antibody confirmed GP88's key role in tumorigenesis. When an anti-GP88 antibody directed to the K19T region of mouse GP88 was added to the culture medium, the growth of highly tumorigenic PC cells was inhibited in a dose dependent fashion (FIG. 2). With reference to FIG. 2, PC cells were cultivated in 96 well plates at a density $2 \times 10^4$ cells/well in DME/F12 medium supplemented with human fibronectin (2 µg/ml) and human transferrin (10 µg/ml). Increasing concentrations of anti-GP88 IgG fraction were added to the wells after the cells were attached. Control cells were treated with equivalent concentrations of non-immune IgG. Two days later, 0.25 mCi of $^3$H-thymidine was added per well for 6 hrs. Cells were then harvested to count $^3$H-thymidine incorporated into DNA as a measure for cell proliferation.

Figure 3:
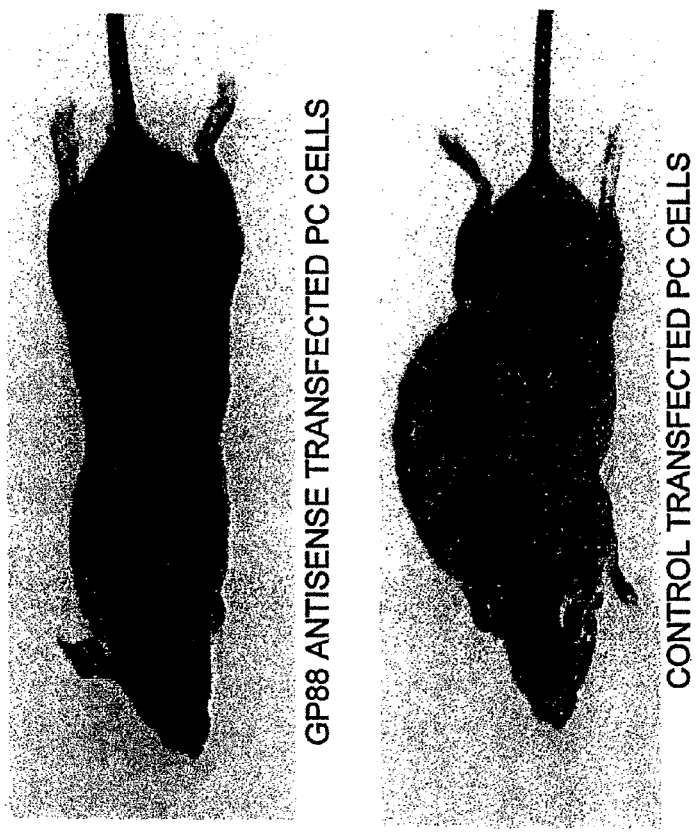
FIG. 3 shows C3H mice injected subcutaneously with $10^6$ antisense GP88 transfected PC cells (bottom) and with empty vector transfected control PC cells (top).

Moreover, when the expression of GP88 was specifically inhibited by antisense GP88 cDNA in PC cells, the production of GP88 was reduced and these PC cells could no longer form tumors in syngeneic C3H mouse. In addition, these PC cells regained responsiveness to insulin. With reference to FIG. 3 and Tables 1 and 2, C3H female mice were injected subcutaneously with $10^6$ antisense GP88 transfected PC cells (as explained below) or $10^6$ empty vector transfected PC cells. Mice were monitored daily for tumor appearance. Photographs were taken 45 days after injection of the cells. The results show that mice injected with antisense GP88 PC cells do not develop tumors, in contrast to the mice injected with empty vector transfected PC cells used as control.

TABLE 1

COMPARISON OF TUMORIGENIC PROPERTIES
OF GP88 ANTISENSE TRANSFECTED CELLS,
CONTROL TRANSFECTED CELLS AND PC CELLS

| CELLS INJECTED | AVERAGE DAY OF TUMOR DETECTION | NUMBER OF MICE WITH TUMORS | AVERAGE TUMOR WEIGHT (g) |
|---|---|---|---|
| PC | 15 ± 3.0 | 5/5 | 9.0 ± 3.2 |
| P14 | 15 ± 3.7 | 5/5 | 7.8 ± 2.7 |
| ASGP88 | — | 0/5 | — |

PC: Control non-transfected cells

P-14: Empty vector control transfected PC cells

ASGP88: PC cells transfected with expression vector containing GP88 antisense cDNA Tumors were excised and weighed at 45 days. — indicates no tumor formation.

TABLE 2

COMPARISON OF PROPERTIES OF 1246,
PC CELLS AND GP88 ANTISENSE CELLS

| 1246 cells | insulin independence PC cells | GP88 antisense transfection Antisense GP 88 cells |
|---|---|---|
| insulin responsive for growth and differentiation | insulin-independent for growth differentiation deficient autocrine production of insulin-related factor | recovery of insulin responsiveness for growth (differentiation?) |
| cell surface insulin receptor expression high | cell surface insulin receptor expression very low | cell surface insulin receptor expression elevated |
| GP88 expression low | GP88 expression constitutively high | GP88 expression inhibited by antisense |
| GP88 expression inhibited by serum | No inhibition by serum | |
| GP88 expression regulated by insulin | GP88 expression constitutive | recovery of insulin regulation for endogenous GP88 expression |
| non-tumorigenic | highly tumorigenic | non-tumorigenic |

Figure 4:
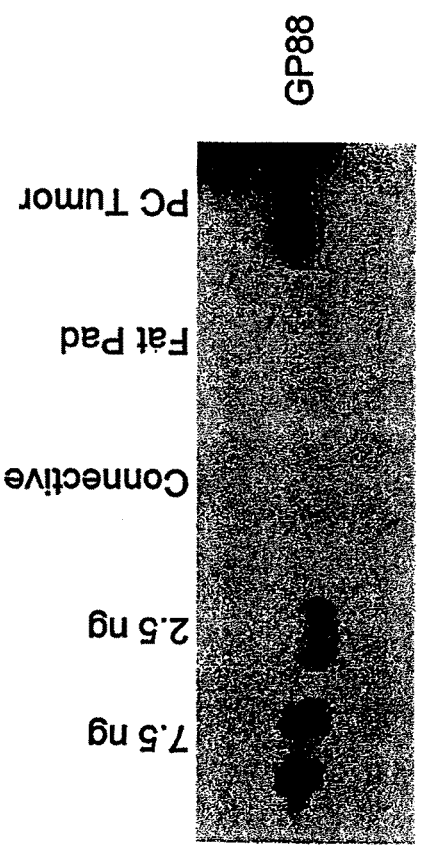
FIG. 4 shows in vivo GP88 expression levels in C3H mice tumor tissues and in surrounding normal tissues.

Comparison of the expression of GP88 indicates that in vivo GP88 levels in tumors is dramatically higher than in normal tissues (FIG. 4). C3H mice were injected with $10^6$ PC cells. Tumor bearing mice were euthanized. Tumors, fat pads and connective tissue were collected. Cell lysates were prepared by incubation in buffer containing detergent as described above for FIG. 1. Protein concentration of tissue extracts was determined, and equivalent amounts of proteins for each sample were analyzed by SDS-PAGE followed by Western blot analysis using anti-GP88 antibody to measure the content of GP88 in tissue extracts. The results showed that the level of GP88 in tumor extracts is at least 10-fold higher than in surrounding connective and fat tissues.

In normal cells (1246 cells, fibroblasts), the expression of GP88 is regulated, in particular by insulin, and inhibited by fetal bovine serum. In tumorigenic cells, a loss of regulation of normal growth leads to the increased expression of GP88 and the acquisition of GP88 dependence for growth. Therefore, inhibition of GP88 expression and/or action is an effective approach to suppression of tumorigenesis. Detection of an elevated GP88 expression in biopsies provides diagnostic analysis of tumors that are responsive to GP88 inhibition therapy.

Figure 6A:
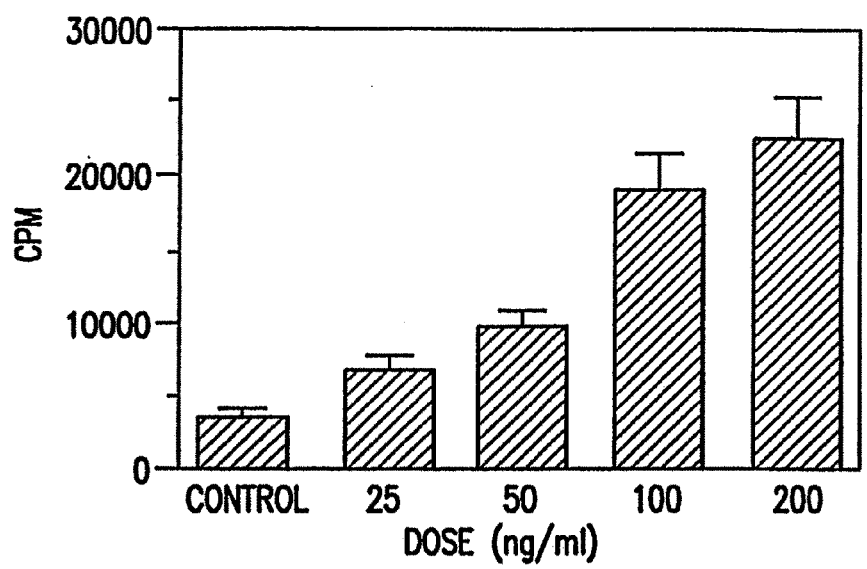
FIG. 6 shows the effect of increasing concentrations of GP88 on the growth of the mouse mammary epithelial cell line C57.
Figure 6B:
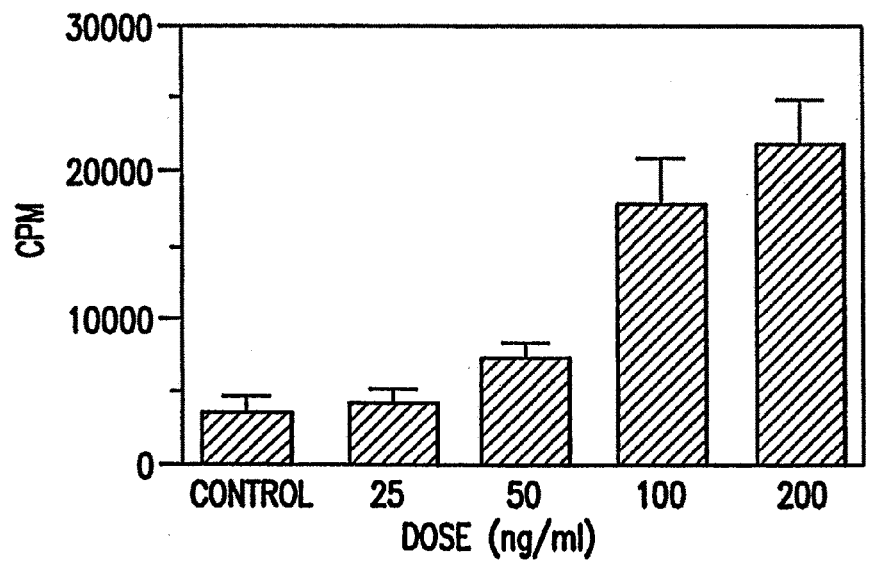
Figure 7:
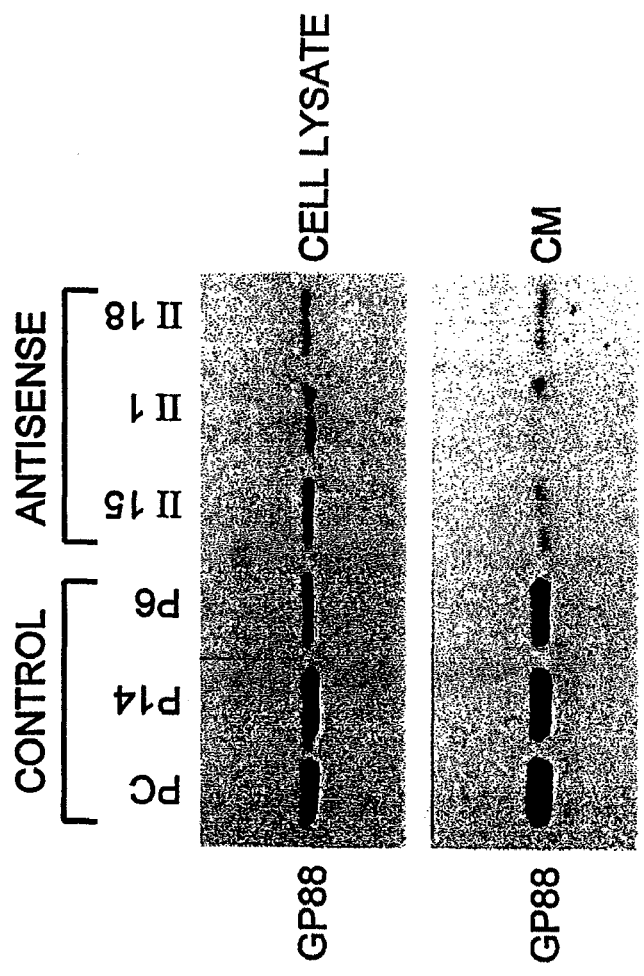
FIG. 7 shows the growth properties and tumorigenic ability of PC cells transfected with a cytomegalovirus promoter controlled expression vector containing GP88 in antisense orientation and PC cells transfected with an empty vector.
Figure 12:
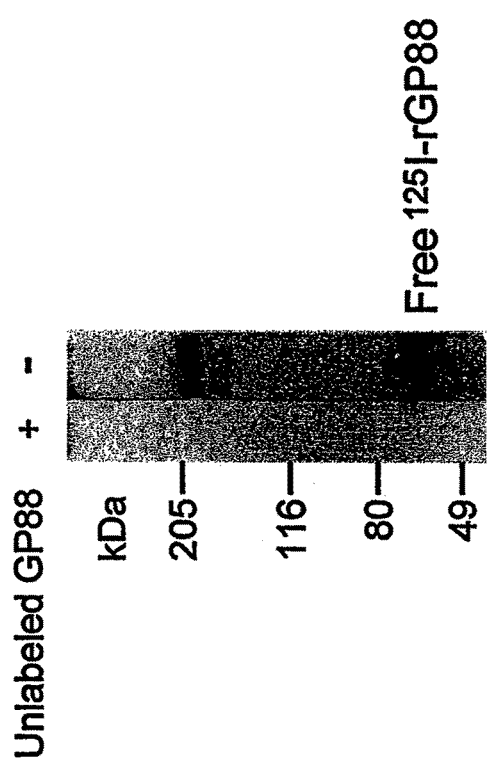
FIG. 12 shows the cross-linking of $^{125}$I-rGP88 to GP88 cell surface receptors on CCL-64 cells. The cross-linking reaction was carried out with disuccinimidyl suberate (DSS). Reaction products were analyzed by SDS-PAGE on a 7% polyacrylamide gel.
Figure 13:
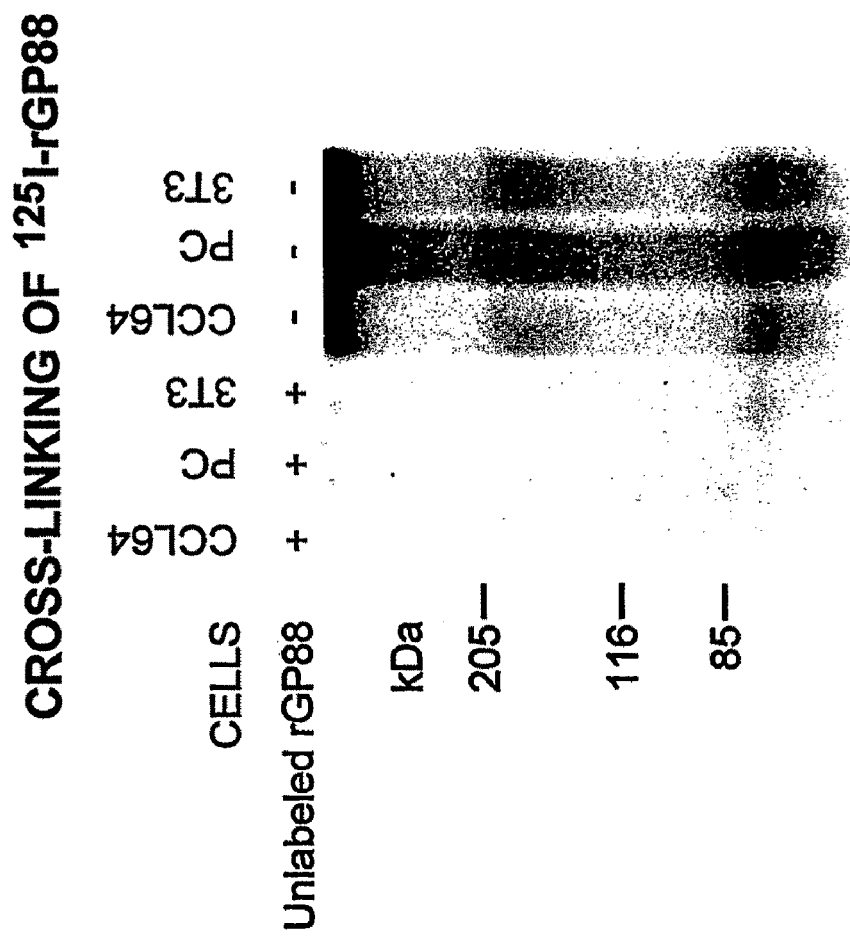
FIG. 13 shows the cross-linking of $^{125}$I-rGP88 to GP88 cell surface receptors on 3T3 fibroblasts, PC cells and C57MG mammary epithelial cells. The results show that these various cell lines display GP88 cell surface receptors of similar molecular weight as the ones on CCL64 cells (FIG. 12).
Figure 14:
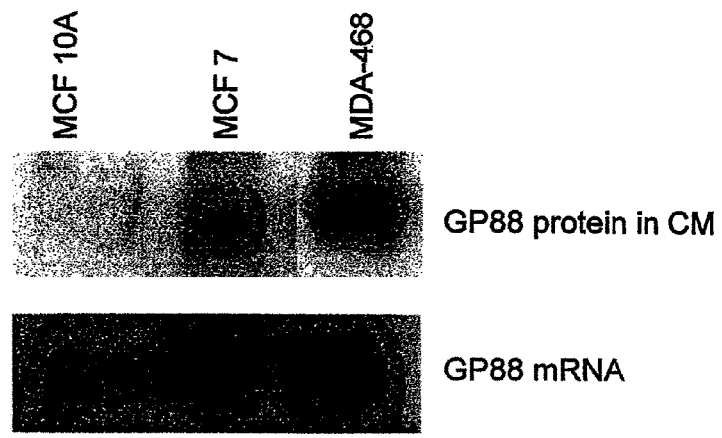
FIG. 14 shows GP88 expression levels in non-tumorigenic MCF 10A and in malignant (MCF 7, MDA-468) human mammary epithelial cells.
Figure 15:
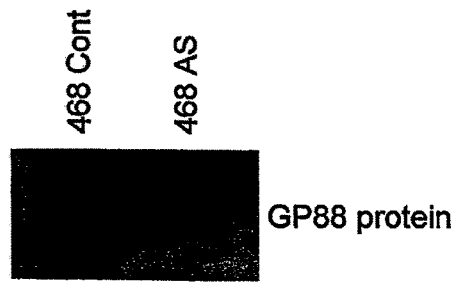
FIG. 15 shows that GP88 expression is inhibited by antisense GP88 cDNA transfection in human breast carcinoma MDA-468 cells.

GP88 is also a tumor-inducing factor in human cancers. As seen in the 1246-3A cell line, a loss of responsiveness to insulin (or to IGF-I) and a concurrent increase in malignancy has been well documented in several human cancers including but not limited to breast cancers. Specifically, breast carcinoma is accompanied by the acquisition of an insulin/IGF-I autocrine loop, which is also the starting point of the development of tumorigenic properties in the mouse model system discussed above. Furthermore, GP88 expression is elevated in human breast carcinomas. More specifically, with reference to FIG. 5, human GP88 was highly expressed in estrogen receptor positive and also in estrogen receptor negative insulin/IGF-I independent highly malignant cells. Also, GP88 is a potent growth factor for mammary epithelial cells (FIG. 6). The data in FIG. 5 was obtained by cultivating MCF7, MDA-MB-453 and MDA-MB-468 cells in DME/F12 medium supplemented with 10% fetal bovine serum (FBS). RNA was extracted from each cell line by the RNAzol method and poly-A$^+$ RNA prepared. GP88 mRNA expression was examined by Northern blot analysis with 3 µg of poly-A$^+$ RNA for each cell line using a $^{32}$P-labeled GP88 cDNA probe.

For Northern blot analysis of GP88 mRNA expression in rodent cells or tissues (mouse and rats), we used a mouse GP88 cDNA probe 311 bp in length starting at nucleotide 551 to 862 (corresponding to amino-acid sequence 160 to 270). RNA can be extracted by a variety of methods (Sambrook™, Molecular Biology manual: 35) well known to people of ordinary skill in the art. The method of choice was to extract RNA using RNAzol (Cinnabiotech) or Trizol (Gibco-BRL) solutions which consists of a single step extraction by guanidinium isothiocyanate and phenol-chloroform.

For Northern blot analysis of GP88 mRNA expression in human cell lines, a 672 bp human GP88 cDNA probe was developed corresponding to nucleotide 1002 to 1674 (corresponding to amino-acid sequence 334-558) of human GP88. See example 8 for a detailed and specific description of the Northern blot analysis method used in the preferred embodiments.

With respect to FIG. 6, C57MG cells were cultivated in the presence of increasing concentrations of GP88 purified from PC cells conditioned medium (top panel), and recombinant GP88 expressed in insect cells (bottom panel), to demonstrate the growth stimulating effect of increasing concentrations of GP88 on the growth of the mouse mammary epithelial cell line C57MG.

A correlation between FIG. 1 autocrine production and increased malignancy has also been well established for glioblastomas, teratocarcinomas and breast carcinomas. In these cancers, GP88 expression is also elevated in human tumors when compared to non-tumorigenic human fibroblasts and other human cell lines. GP88 promotes the growth of mammary carcinoma cells.

Anti-GP88 Antibodies

The invention provides compositions for treating and diagnosing diseases linked to increased expression of GP88. This also will apply to treatment and diagnosis of diseases linked to increased responsiveness to GP88. The compositions of this invention include anti-GP88 antibodies which neutralize the biological activity of GP88.

The present invention is also directed to an antibody specific for an epitope of GP88 and the use of such antibody to detect the presence or measure the quantity or concentration of GP88 molecule, a functional derivative thereof or a homologue from different animal species in a cell, a cell or tissue extract, culture medium or biological fluid. Moreover, anti-GP88 antibody can be used to target cytotoxic molecules to a specific site.

For use as antigen for development of antibodies, the GP88 protein naturally produced or expressed in recombinant form or functional derivative thereof, preferably having at least 9 amino-acids, is obtained and used to immunize an animal for production of polyclonal or monoclonal antibody. An antibody is said to be capable of binding a molecule if it is capable of reacting with the molecule to thereby bind the molecule to the antibody. The specific reaction is meant to indicate that the antigen will react in a highly selective manner with its corresponding antibody and not with the multitude of other antibodies which may be evoked by other antigens.

The term antibody herein includes but is not limited to human and non-human polyclonal antibodies, human and non-human monoclonal antibodies (mAbs), chimeric antibodies, anti-idiotypic antibodies (anti-IdAb) and humanized antibodies. Polyclonal antibodies are heterogeneous populations of antibody molecules derived either from sera of animals immunized with an antigen or from chicken eggs. Monoclonal antibodies ("mAbs") are substantially homogeneous populations of antibodies to specific antigens. mAbs may be obtained by methods known to those skilled in the art (U.S. Pat. No. 4,376,110). Such antibodies may be of any immunological class including IgG, IgM, IgE, IgA, IgD and any subclass thereof. The hybridoma producing human and non-human antibodies to GP88 may be cultivated in vitro or in vivo. For production of a large amount of mAbs, in vivo is the presently preferred method of production. Briefly, cells from the individual hybridomas are injected intraperitoneally into pristane primed Balb/c mice or Nude mice to produce ascites fluid containing high concentrations of the desired mAbs. mAbs may be purified from such ascites fluids or from culture supernatants using standard chromatography methods well known to those of skill in the art.

Human monoclonal Ab to human GP88 can be prepared by immunizing transgenic mice expressing human immunoglobulin genes. Hybridoma produced by using lymphocytes from these transgenic animals will produce human immunoglobulin instead of mouse immunoglobulin.

Since most monoclonal antibodies are derived from murine source and other non-human sources, their clinical efficiency may be limited due to the immunogenicity of rodent mAbs administered to humans, weak recruitment of effector function and rapid clearance from serum. To circumvent these problems, the antigen-binding properties of murine antibodies can be conferred to human antibodies through a process called humanization. A humanized antibody contains the amino-acid sequences for the 6 complementarity-determining regions (CDRs) of the parent murine mAb which are grafted onto a human antibody framework. The low content of non-human sequences in humanized antibodies (around 5%) has proven effective in both reducing the immunogenicity and prolonging the serum half life in humans. Methods such as the ones using monovalent phage display and combinatorial library strategy for humanization of monoclonal antibodies are now widely applied to the humanization of a variety of antibodies and are known to people skilled in the art. These humanized antibodies and human antibodies developed with transgenic animals as described above are of great therapeutic use for several diseases including but not limited to cancer.

Hybridoma supernatants and sera are screened for the presence of antibody specific for GP88 by any number of immunoassays including dot blots and standard immunoassays (EIA or ELISA) which are well known in the art. Once a supernatant has been identified as having an antibody of interest, it may be further screened by Western blotting to identify the size of the antigen to which the antibody binds. One of ordinary skill in the art will know how to prepare and screen such hybridomas without undue experimentation in order to obtain a desired polyclonal or mAb.

Chimeric antibodies have different portions derived from different animal species. For example, a chimeric antibody might have a variable region from a murine mAb and a human immunoglobulin constant region. Chimeric antibodies and methods for their production are also known to those skilled in the art.

Accordingly, mAbs generated against GP88 may be used to induce human and non-human anti-IdAbs in suitable animals. Spleen cells from such immunized mice are used to produce hybridomas secreting human or non-human anti-Id mAbs. Further, the anti-Id mAbs can be coupled to a carrier such as Keyhole Limpet Hemocyanin (KLH) or bovine serum albumin (BSA) and used to immunize additional mice. Sera from these mice will contain human or non-human anti-anti-IdAb that have the binding properties of the original mAb specific for a GP88 polypeptide epitope. The anti-Id mAbs thus have their own idiotypic epitopes or idiotypes structurally similar to the epitope being evaluated.

The term antibody is also meant to include both intact molecules as well as fragments thereof such as, for example, Fab and F(ab')2, which are capable of binding to the antigen. Fab and F(ab')2 fragments lack the Fc fragment of intact antibody, clear more rapidly from the circulation and may have less non-specific tissue binding than an intact antibody. Such fragments are typically produced by proteolytic cleavage, using enzymes such as papain (to generate Fab fragments) and pepsin (to generate F(ab')2 fragments). It will be appreciated that Fab and F(ab')2 and other fragments of the antibodies useful in the present invention may be used for the detection or quantitation of GP88, and for treatment of pathological states related to GP88 expression, according to the methods disclosed herein for intact antibody molecules.

According to the present invention, antibodies that neutralize GP88 activity in vitro can be used to neutralize GP88 activity in vivo to treat diseases associated with increased GP88 expression or increased responsiveness to GP88, such as but not limited to multiple myeloma. A subject, preferably a human subject, suffering from multiple myeloma or other disease associated with increased GP88 expression is treated with an antibody to GP88. Such treatment may be performed in conjunction with other anti-cancer or anti-viral therapy. A typical regimen comprises administration of an effective amount of the antibody specific for GP88 administered over a period of one or several weeks and including between about one and six months. The antibody of the present invention may be administered by any means that achieves its intended purpose. For example, administration may be by various routes including but not limited to subcutaneous, intravenous, intradermal, intramuscular, intraperitoneal and oral. Parenteral administration can be by bolus injection or by gradual perfusion over time. Preparations for parenteral administration include sterile aqueous or non-aqueous solutions, suspensions and emulsions, which may contain auxiliary agents or excipients known in the art. Pharmaceutical compositions such as tablets and capsules can also be prepared according to routine methods. It is understood that the dosage of will be dependent upon the age, sex and weight of the recipient, kind of concurrent treatment, if any, frequency of treatment and the nature of the effect desired. The ranges of effective doses provided below are not intended to limit the invention and merely represent preferred dose ranges. However the most preferred dosage will be tailored to the individual subject as is understood and determinable by one skilled in the art. The total dose required for each treatment may be administered by multiple doses or in a single dose. Effective amounts of antibody are from about 0.01 µg to about 100 mg/kg body weight and preferably from about 10 µg to about 50 mg/kg. Antibody may be administered alone or in conjunction with other therapeutics directed to the same disease.

According to the present invention and concerning the neutralizing antibody, GP88 neutralizing antibodies can be used in all therapeutic cases where it is necessary to inhibit GP88 biological activity, even though there may not necessarily be a change in GP88 expression, including cases where there is an overexpression of GP88 cell surface receptors and this in turn results in an increased biological activity, or where there is an alteration in GP88 signaling pathways or receptors leading to the fact that the signaling pathways are always "turned on." In one embodiment, the GP88 neutralizing antibodies are used to inhibit the growth of multiple myeloma cells. Neutralizing antibodies to growth factor and to growth factor receptors have been successfully used to inhibit the growth of cells whose proliferation is dependent on this growth factor. This has been the case for IGF-I receptor in human breast carcinoma cells and bombesin for lung cancer. The antibody to GP88 can also be used to deliver compounds such as, but not limited to, cytotoxic reagents such as toxins, oncotoxins, mitotoxins and immunotoxins, or antiseuse oligonucleotides, in order to specifically target them to cells expressing or responsive to GP88.

One region that allows antigen to develop a neutralizing antibody to GP88 is the 19 amino-acid region defined as K19T in the mouse GP88, and E19V in the human GP88 which is not located within the epithelin/granulin 6 kDa repeats but between these repeats, specifically between granulin A (epithelin 1) and granulin C in what is considered a variant region (see FIG. 10). Without wishing to be bound by theory, it is believed that the region important for the biological activity of GP88 lies outside of the epithelin repeats.

The antibodies or fragments of antibodies useful in the present invention may also be used to quantitatively or qualitatively detect the presence of cells which express the GP88 protein. This can be accomplished by immunofluorescence techniques employing a fluorescently labeled antibody (see below) with fluorescent microscopic, flow cytometric, or fluorometric detection. The reaction of antibodies and polypeptides of the present invention may be detected by immunoassay methods well known in the art.

The antibodies of the present invention may be employed histologically as in light microscopy, immunofluorescence or immunoelectron microscopy, for in situ detection of the GP88 protein in tissues samples or biopsies. In situ detection may be accomplished by removing a histological specimen from a patient and applying the appropriately labeled antibody of the present invention. The antibody (or fragment) is preferably provided by applying or overlaying the labeled antibody (or fragment) to the biological sample. Through the use of such a procedure, it is possible to determine not only the presence of the GP88 protein but also its distribution in the examined tissue. Using the present invention, those of ordinary skill in the art will readily perceive that any wide variety of histological methods (such as staining procedures) can be modified in order to achieve such in situ detection.

Assays for GP88 typically comprise incubating a biological sample such as a biological fluid, a tissue extract, freshly harvested or cultured cells or their culture medium in the presence of a detectably labeled antibody capable of identifying the GP88 protein and detecting the antibody by any of a number of techniques well known in the art.

The biological sample may be treated with a solid phase support or carrier such as nitrocellulose or other solid support capable of immobilizing cells or cell particles or soluble proteins. The support may then be washed followed by treatment with the detectably labeled anti-GP88 antibody. This is followed by wash of the support to remove unbound antibody. The amount of bound label on said support may then be detected by conventional means. By solid phase support is intended any support capable of binding antigen or antibodies such as but not limited to glass, polystyrene polypropylene, nylon, modified cellulose, or polyacrylamide.

The binding activity of a given lot of antibody to the GP88 protein may be determined according to well known methods. Those skilled in the art will be able to determine operative and optimal assay conditions for each determination by employing routine experimentation.

Detection of the GP88 protein or functional derivative thereof and of a specific antibody for the protein may be accomplished by a variety of immunoassays well known in the art such as enzyme linked immunoassays (EIA) or radio-immunoassays (RIA). Such assays are well known in the art and one of skill will readily know how to carry out such assays using the anti-GP88 antibodies and GP88 protein of the present invention.

Such immunoassays are useful to detect and quantitate GP88 protein in serum or other biological fluid as well as in tissues, cells, cell extracts, or biopsies. In a preferred embodiment, the concentration of GP88 is measured in a tissue specimen as a means for diagnosing cancer or other disease associated with increased expression of GP88.

The presence of certain types of cancers (e.g., multiple myeloma) and the degree of malignancy are said to be "proportional" to an increase in the level of the GP88 protein. The term "proportional" as used herein is not intended to be limited to a linear or constant relationship between the level of protein and the malignant properties of the cancer. The term "proportional" as used herein, is intended to indicate that an increased level of GP88 protein is related to appearance, recurrence or display of malignant properties of a cancer or other disease associated with increased expression of GP88 at ranges of concentration of the protein that can be readily determined by one skilled in the art.

Another embodiment of the invention relates to evaluating the efficacy of anti-cancer or anti-viral drug or agent by measuring the ability of the drug or agent to inhibit the expression or production of GP88. The antibodies of the present invention are useful in a method for evaluating anti-cancer or anti-viral drugs in that they can be employed to determine the amount of the GP88 protein in one of the above-mentioned immunoassays. Alternatively, the amount of the GP88 protein produced is measured by bioassay (cell proliferation assay) as described herein. The bioassay and immunoassay can be used in combination for a more precise assessment.

An additional embodiment is directed to an assay for diagnosing cancers or other diseases associated with an increase in GP88 expression based on measuring in a tissue or biological fluid the amount of mRNA sequences present that encode GP88 or a functional derivative thereof, preferably using an RNA-DNA hybridization assay. The presence of certain cancers and the degree of malignancy is proportional to the amount of such mRNA present. For such assays the source of mRNA will be biopsies and surrounding tissues. The preferred technique for measuring the amount of mRNA is a hybridization assay using DNA of complementarity base sequence.

Another related embodiment is directed to an assay for diagnosing cancers or other diseases associated with an increase in GP88 responsiveness based on measuring on a tissue biopsy whether treatment with anti-GP88 neutralizing antibody will inhibit its growth or other biological activity.

Another related embodiment is a method for measuring the efficacy of anti-cancer or anti-viral drug or agent which comprises the steps of measuring the agent's effect on inhibiting the expression of mRNA for GP88. Similarly such method can be used to identify or evaluate the efficacy of GP88 antagonizing agents by measuring the ability of said agent to inhibit the production of GP88 mRNA.

Nucleic acid detection assays, especially hybridization assays, can be based on any characteristic of the nucleic acid molecule such as its size, sequence, or susceptibility to digestion by restriction endonucleases. The sensitivity of such assays can be increased by altering the manner in which detection is reported or signaled to the observer. A wide variety of labels have been extensively developed and used by those of ordinary skill in the art, including enzymatic, radio-isotopic, fluorescent, chemical labels and modified bases.

One method for overcoming the sensitivity limitation of a nucleic acid for detection is to selectively amplify the nucleic acid prior to performing the assay. This method has been referred as the "polymerase chain reaction" or PCR (U.S. Pat. Nos. 4,683,202 and 4,582,788). The PCR reaction provides a method for selectively increasing the concentration of a particular nucleic acid sequence even when that sequence has not been previously purified and is present only in a single copy in a particular sample.

GP88 Antisense Components

This invention also provides GP88 antisense components. The constitutive expression of antisense RNA in cells has been shown to inhibit the expression of more than 20 genes and the list continues to grow. Possible mechanisms for antisense effects are the blockage of translation or prevention of splicing, both of which have been observed in vitro. Interference with splicing allows the use of intron sequences which should be less conserved and therefore result in greater specificity, inhibiting expression of a gene product of one species but not its homologue in another species. Alternatively, nucleic acid sequences which inhibit or interfere with gene expression (e.g., RNAi, ribozymes, aptamers) can be used to inhibit or interfere with the activity of RNA or DNA encoding GP88.

The term antisense component corresponds to an RNA sequence as well as a DNA sequence coding therefor, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. The action of the antisense RNA results in specific inhibition of gene expression in the cells.

According to the present invention, transfection of B-cell leukemia cells with DNA antisense to the GP88 cDNA inhibits its endogenous GP88 expression and inhibits tumorigenicity of the antisense cDNA transfected cells. This antisense DNA must have sufficient complementarity, about 18-30 nucleotides in length, to the GP88 gene so that the antisense RNA can hybridize to the GP88 gene (or mRNA) and inhibit GP88 gene expression regardless of whether the action is at the level of splicing, transcription, or translation. The degree of inhibition is readily discernible to one skilled in the art without undue experimentation given the teachings herein and preferably is sufficient to inhibit the growth of cells whose proliferation is dependent on the expression of GP88. One of ordinary skill in the art will recognize that the antisense RNA approach is but a number of known mechanisms which can be employed to block specific gene expression.

The antisense components of the present invention may be hybridizable to any of several portions of the target GP88 cDNA, including the coding sequence, 3' or 5' untranslated regions, or other intronic sequences, or to GP88 mRNA. As is readily discernible by one of ordinary skill in the art, the minimal amount of homology required by the present invention is that sufficient to result in hybridization to the GP88 DNA or mRNA and in inhibition of transcription of the DNA, or translation or function of the mRNA, preferably without affecting the function of other mRNA molecules and the expression of other unrelated genes.

Antisense RNA is delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. Stable transfection of various antisense expression vectors containing GP88 cDNA fragments in the antisense orientation have been performed. One can also deliver antisense components to cells using a retroviral vector. Delivery can also be achieved by liposomes.

For purpose of antisense technology for in vivo therapy, the currently preferred method is to use antisense oligonucleotides, instead of performing stable transfection of an antisense cDNA fragment constructed into an expression vector. Antisense oligonucleotides having a size of 15-30 bases in length and with sequences hybridizable to any of several portions of the target GP88 cDNA, including the coding sequence, 3' or 5' untranslated regions, or other intronic sequences, or to GP88 mRNA, are preferred. Sequences for the antisense oligonucleotides to GP88 are preferably selected as being the ones that have the most potent antisense effects. Factors that govern a target site for the antisense oligonucleotide sequence are related to the length of the oligonucleotide, binding affinity, and accessibility of the target sequence. Sequences may be screened in vitro for potency of their antisense activity by measuring inhibition of GP88 protein translation and GP88 related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides.

The preferred GP88 antisense oligonucleotides are those oligonucleotides which are stable, have a high resilience to nucleases (enzymes that could potentially degrade oligonucleotides), possess suitable pharmacokinetics to allow them to traffic to disease tissue at non-toxic doses, and have the ability to cross through plasma membranes.

Phosphorothioate antisense oligonucleotides may be used. Modifications of the phosphodiester linkage as well as of the heterocycle or the sugar may provide an increase in efficiency. With respect to modification of the phosphodiester linkage, phosphorothioate may be used. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo. Cell culture and in vivo tumor experiments using these types of oligonucleotides targeted to c-raf-1 resulted in enhanced potency.

The delivery route will be the one that provides the best antisense effect as measured according to the criteria described above. In vitro cell culture assays and in vivo tumor growth assays using antisense oligonucleotides have shown that delivery mediated by cationic liposomes, by retroviral vectors and direct delivery are efficient. Another possible delivery mode is targeting using antibody to cell surface markers for the tumor cells. Antibody to GP88 or to its receptor may serve this purpose.

Inhibiting The Growth of Hematopoietic Malignant Cells

Preferred embodiments of the invention are directed to methods and compositions for reducing, interfering with, and/or inhibiting the growth and proliferation of hematopoietic malignant cells. Hematopoietic cells are divided into three categories: erythroid, myeloid and lymphoid cells. The erythroid cells are red blood cells and their precursors. Myeloid cells include monocytes, granulocytes, basophils, eosinophils and megakaryocytes. Myeloma is a type of cancer originating from myeloid cells (monocytes). Hematopoietic malignant cells include, but are not limited to leukemias (e.g., ALL (Acute lymphoblastic leukemia), AML (acute myelogenous leukemia), CML (chronic myelogenous leukemia), acute bilineage leukemia, acute undifferentiated leukemia, chronic lymphocytic leukemia, juvenile chronic myelogenous leukemia, prolymphocytic leukemia, MDS (myelodysplastic syndromes), acquired idiopathic sideroblastic anemia, acute myelofibrosis, chronic myelomonocytic leukemia, essential thrombocythemia, myelodysplastic disorders, myelofibrosis myeloid metaplasia, paroxysmal nocturnal hemoglobinuria, polycythemia vera, refractory anemia, refractory anemia with excess blasts (RAEB), refractory anemia with excess blasts in transformation (RAEB-T)), and lymphomas (e.g., Hodgkin lymphoma, non-Hodgkin lymphoma, plasma cell dyscrasia, multiple myeloma, plasma cell leukemia, waldenstrom macroglobulinemia).

As described above, hematopoietic malignant cells express elevated levels of GP88. The present invention demonstrates that GP88 is the first growth factor shown to be a prognostic indicator of hematopoietic malignancies (e.g., B-cell leukemias such as multiple myeloma), and that GP88 antagonists reduce, inhibit, and/or interfere with the growth of hematopoietic malignant cells.

Figure 16:
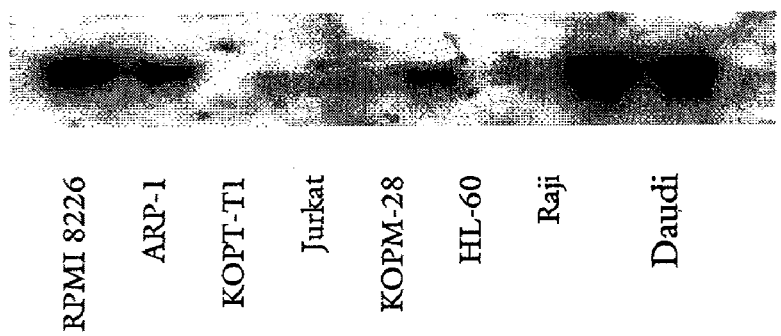
FIG. 16 shows GP88 protein expression in various human hematological cell lines. GP88 is expressed in human multiple myeloma cell lines ARP-1 and RPMI 8226, human B cell lines Raji and Daudi, human macrophage cell line KOPM28, but not in human T cell lines Jurkat and KOPT-K1.
Figure 17:
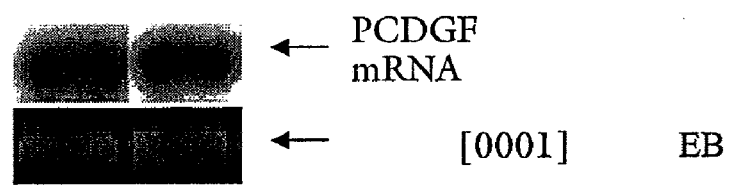
FIG. 17 shows that GP88 mRNA is expressed in human multiple myeloma cell lines ARP-1 and RPMI 8226.
Figure 18A:
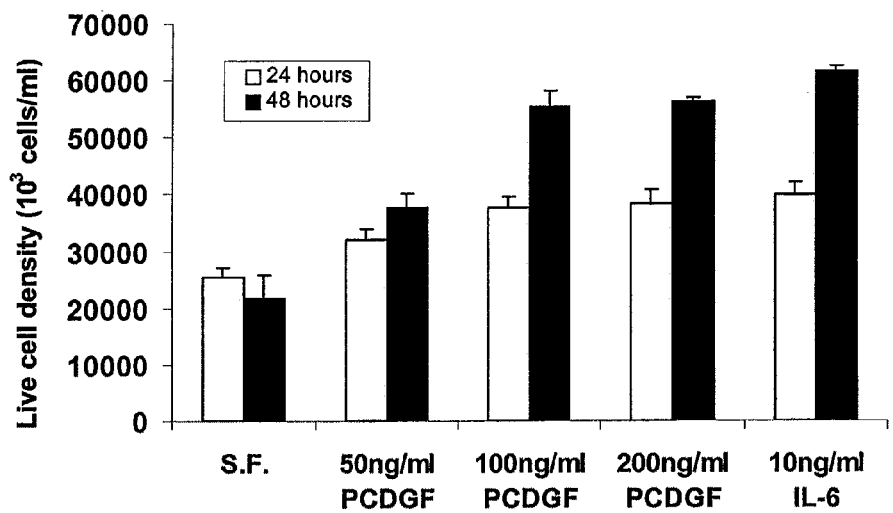
FIGS. 18A and 18B show the effect of GP88 protein on the growth of RPMI 8226 cells.
Figure 18B:
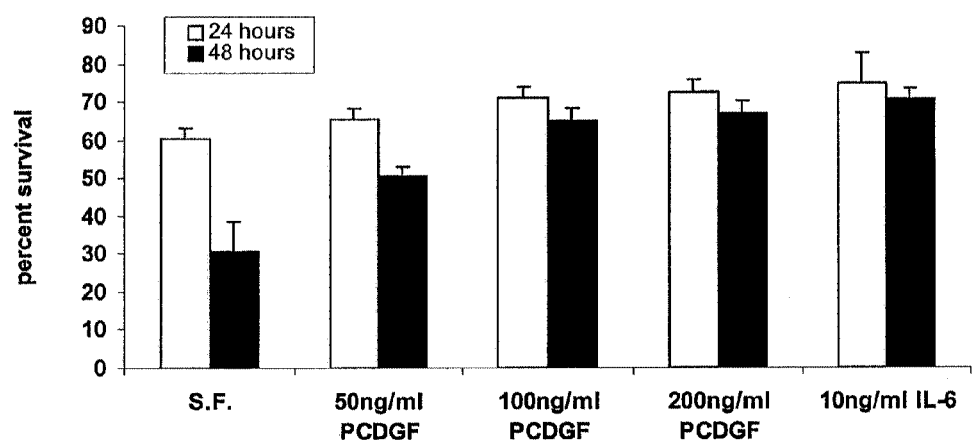
Figure 19A:
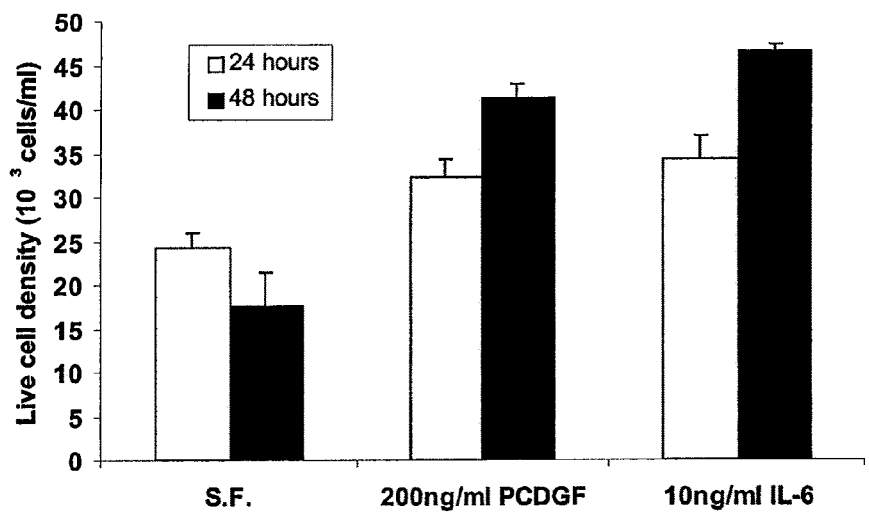
FIGS. 19A and 19B show the effect of GP88 on the growth of ARP-1 cells.
Figure 19B:
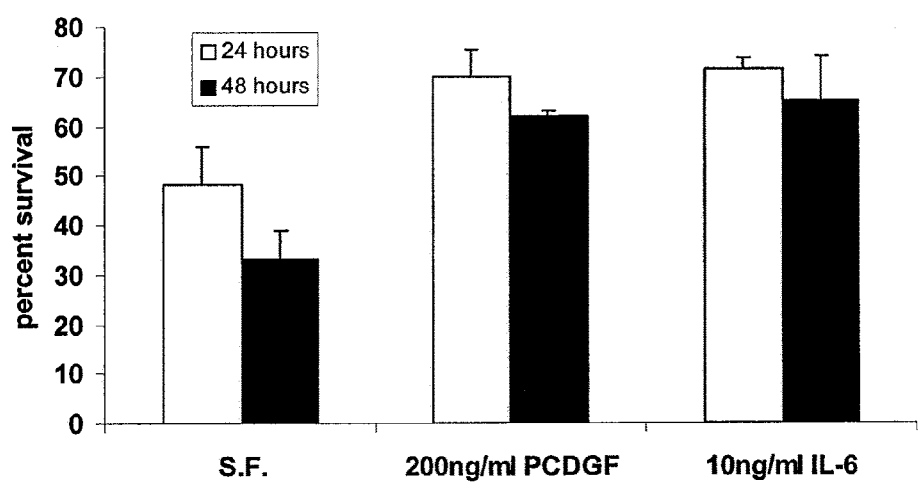

As shown in FIGS. 16 and 17, GP88 protein (FIG. 16) and mRNA (FIG. 17) is overexpressed in human multiple myeloma cell lines ARP-1 and RPMI 8226 and human B cell lines Raji and Daudi and not expressed in human T-cell lines Jurkat and KOPTI-K1. In addition, GP88 stimulates growth and increases the percent survival of multiple myeloma cells. The live cell density (i.e., growth) and viability of RPMI 8226 multiple myeloma cells increased in a dose dependant manner in response to increased amounts of GP88 (FIGS. 18A and 18B). As shown in FIG. 18A, the live cell density of RPMI 8226 cells increased by 3-fold in the presence of 200 ng/ml of GP88. Likewise, the percent survival of RPMI 8226 cells increased by 2-fold after 48 hours in the presence of 100 or 200 ng/ml of GP88. The growth and viability response of RPMI 8226 myeloma cells to GP88 is similar to that of myeloma cells to IL-6 (compare FIG. 18A col. 3 to col. 4 and FIG. 18B col. 3 to col. 4). Similar results were obtained with ARP-1 multiple myeloma cells. The live cell density of ARP-1 cells more than doubled in the presence of 200 ng/ml of GP88. (FIG. 19A). The percent survival of ARP-1 multiple myeloma cells doubled after 48 hours in the presence of 200 ng/ml of GP88. IL-6 also doubled both the live cell density and percent survival after 48 hours of ARP-1 cells. (FIGS. 19A and 19B). Reducing, inhibiting, or interfering with the growth stimulatory and survival effects of GP88 on myeloma cells reduces the growth and survival of multiple myeloma cells, providing a therapeutic benefit to multiple myeloma patients.

In one embodiment of the invention, a method of inhibiting, reducing, or interfering with the growth of hematopoietic malignant cells (e.g., B-cell leukemias cells such as myeloma cells) by contacting hematopoietic malignant cells with a GP88 antagonist is provided. As described above, GP88 antagonists (e.g., anti-GP88 antibodies) inhibit the growth of myeloma cells. In another embodiment of the invention, the hematopoietic malignant cells are human myeloma cells.

GP88 antagonists (e.g., anti-GP88 antibodies or antibody fragments, and GP88 small molecules) bind to GP88 secreted from the cell and inhibit and/or interfere with the biological activity of GP88. GP88 antagonists can, for example, bind to GP88 and prevent GP88 from binding to its receptor on the cell surface. GP88 antagonists (e.g., anti-GP88 antisense polynucleotides) can also enter the cell and inhibit or interfere with the expression of the GP88 protein. For example, anti-GP88 antisense polynucleotides can hybridize with mRNA encoding GP88 and block translation of the GP88 protein. Alternatively, the GP88 antagonist may be conjugated or linked to another molecule capable of interfering or inhibiting cell growth (e.g., toxins, antibodies, antibody fragments, and nucleic acids). GP88 antagonists also can interfere with the biological activity of GP88 by binding to a molecule other than GP88. For example, GP88 antagonists can bind to, inhibit, and/or interfere with the activity of the GP88 receptor and thus interfere with the binding of GP88 to its receptor.

The term "GP88 antagonist" refers to any composition that inhibits or blocks GP88 expression, production or secretion, or any composition that inhibits or blocks the biological activity of GP88 including, but not limited to, anti-GP88 antibodies, anti-GP88 antisense polynucleotides, anti-GP88 receptor antibodies, anti-GP88 small molecules. In one embodiment of the invention, the GP88 antagonist is an anti-GP88 antibody or antibody fragment. The term "antibody fragment" refers to any section, portion, or part of an antibody that retains the antigen binding properties of the antibody. Anti-GP88 antibodies also include antibody fragments, humanized antibodies, humanized antibody fragments and can be made as described above.

The term "contacting" refers to delivering GP88 antagonist to hematopoietic malignant cells (e.g., leukemia cells of B-cell lineage) wherein the GP88 antagonist can interact with the cell either directly (e.g., binding to GP88 inside the cell) or indirectly (e.g., binding to GP88 and preventing GP88 from directly contacting myeloma cells). A GP88 antagonist may be injected into the blood stream of a patient suffering from a hematopoietic malignancy to bind GP88 and prevent GP88 from stimulating hematopoietic malignant cell growth. GP88 antagonist may also be microinjected into a cell by shooting pellets coated with GP88 antagonist inside the cell in order to prevent secretion of GP88. Hematopoietic malignant cells may also be transfected with nucleic acid encoding a GP88 antagonist. Alternatively, patients can be treated with a GP88 small molecule antagonist to block GP88 activity. Contacting hematopoietic malignant cells with GP88 antagonist blocks the activity of GP88 and therefore inhibits, reduces, and/or interferes with the growth of the cells. GP88 antagonists such as anti-GP88 antibodies and anti-GP88 antisense nucleic acids can be made and administered by any suitable mechanism (e.g., injection, and aerosol) as described above.

Figure 20:
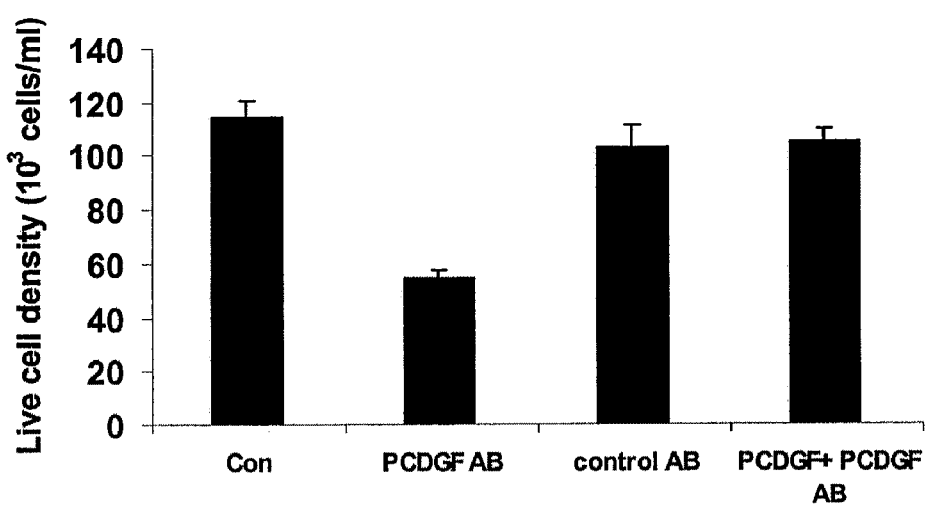
FIG. 20 shows the effect of anti-GP88 neutralizing antibody on the growth of RPMI 8226 cells. Treatment of RPMI 8226 cells with anti-GP88 antibody inhibited cell growth by 50% compared to cells that did not receive GP88 antibody (control AB) or cells treated with a combination of GP88 and anti-GP88 antibody.

Administration of GP88 antagonists to hematopoietic malignant cells significantly reduces the growth of the cells. For example, anti-GP88 neutralizing antibody inhibits the growth of RPMI 8226 multiple myeloma cells by about 50% while treatment of the same cells with non-immuno rabbit IgG did not show any significant inhibition of cell growth. (FIG. 20). Addition of exogenous GP88 reversed the inhibitory effect of the anti-GP88 neutralizing antibody. (FIG. 20). The reversal of GP88 antagonist induced growth inhibition by the addition of exogenous GP88 demonstrates that GP88 is a growth factor for myeloma cells. The growth of myeloma cells can be measured by several methods including, but not limited to, measuring the live cell density in vitro by staining cells with trypan blue, uptake of radioactive nucleotides, cell mass, BudR incorporation, ELISA, cell metabolism, spectroscopy, and direct measurement of the dimensions of a tumor mass.

Preferred embodiments of the invention are also directed to methods of diagnosing B-cell leukemia by detecting GP88 in tissue samples containing B-cells (e.g., blood, bone marrow, lymph, spleen, liver). The presence of GP88 in tissue samples containing B-cells indicates B-cell leukemia. GP88 protein or nucleic acid can be detected as described above. Also provided are methods of diagnosing B-cell leukemia by detecting the presence of GP88 in B-cells. The presence of GP88 in B-cells indicates B-cell leukemia.

In another embodiment of the invention, the presence of GP88 in bone marrow cells indicates the presence of multiple myeloma cells. The presence of immunoglobulin lambda or kappa light chains in bone marrow cells is a marker for neoplastic or potentially neoplastic myeloma cells. Hitzman et al., *Immunoperoxidase staining of bone marrow sections, Cancer* 48(11):2438-46 (1981). Immunostaining bone marrow sections for the presence of lambda or kappa immunoglobulin light chains allows for detection of myeloma cases that are difficult to diagnose such as nonsecretory myeloma. Id. As shown in Table 1, such myeloma cells that stain positive for kappa or lambda light chains also stain positive for GP88.

TABLE 1

Expression of Ig light chain and GP88 in bone marrow smears From multiple myeloma patients

| Patients | Ig κ chain | Ig λ chain | GP88 |
|---|---|---|---|
| 1 | + | − | + |
| 2 | − | − | − |
| 3 | − | + | + |
| 4 | + | − | + |
| 5a | − | − | − |
| 5b | + | − | + |
| 6 | − | − | − |
| 7 | − | + | + |
| 8 | + | − | + |
| 9 | − | − | − |
| 10 | + | − | + |
| 11 | + | − | + |
| 12 | + | − | + |

Figure 25A:
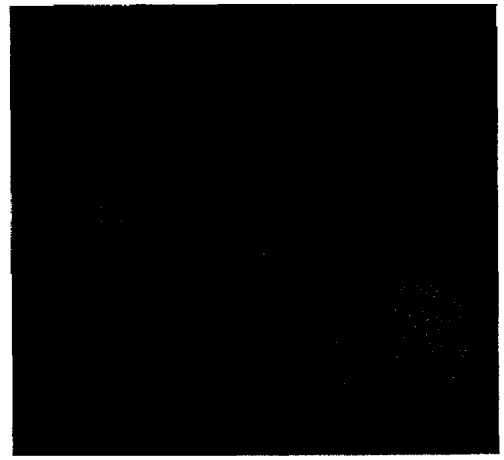
FIGS. 25A, 25B, and 25C show the results of triple-stained bone marrow smears from multiple myeloma patients. The bone marrow smears were stained for the presence of GP88 and for markers of the kappa and lambda light chains. The bone marrow smears were stained with DAPI (FIG. 25A), anti-human kappa/lambda chain antibody (FIG. 25B), and anti-GP88 antibody (25C).
Figure 25B:
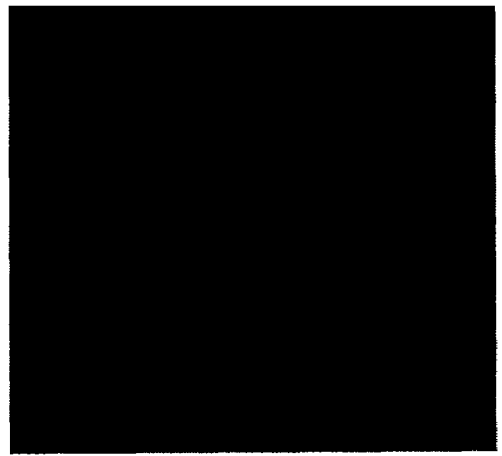
Figure 25C:
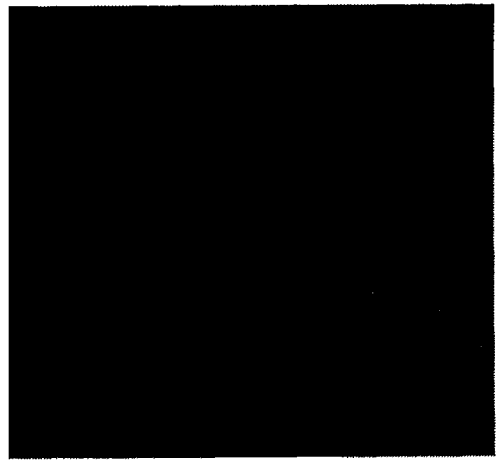

GP88 is not detected in bone marrow cells from patients in remission or in cells that do not express kappa or lambda immunoglobulin light chains. Furthermore, patients in remission for multiple myeloma (e.g., Patient 5a) do not express GP88. Patient 5a relapsed and displayed the symptoms of multiple myeloma (Patient 5b). Patient 5b was positive for both the kappa light chain and GP88. Thus, GP88 serves as a biological marker for multiple myeloma. An example of a triple stain for the presence of a control (DAPI), kappa/lambda light chains, and GP88 in the same patient sample is shown in FIGS. 25A, 25B, and 25C respectively. Detecting the presence of GP88 in bone marrow cells is indicative of whether multiple myeloma cells are present. The presence of GP88 can be detected by GP88 antagonists (e.g., anti-GP88 antibodies, anti-GP88 nucleic acid) using a variety of methodologies including, but not limited to, immunostaining, immunofluorescence, in situ hybridization, western blot, northern blot, and southern blot.

The Presence of GP88 Indicates Whether a Patient is Responding or Responsive to Anti-Cancer Therapy Anti-cancer agents such as glucocorticoids and glucocorticoid analogs (e.g., dexamethasone, prednisolone, methylprednisolone, hydrocortisone, betamethasone, prednisone, fludrocortisone, cortisone, corticosterone, triamcinolone, and paramethasone) alone or in combination with chemotherapy (e.g., alkylating agents) are used to treat patients with hematopoietic malignancies (e.g., B-cell leukemia). However, certain patients may not be responsive to anti-cancer therapy. In addition, it is well known that patients that are initially responsive to anti-cancer therapy develop resistance and no longer respond to the drugs.

For example, prolonged systemic exposure to glucocorticoids may have severe adverse side effects such as: (1) endocrine and metabolic disturbances including, but not limited to, Cushing-like syndrome, hirsutism, menstrual irregularities, premature epiphyseal closure, secondary adrenocortical and pituitary unresponsiveness, decreased glucose tolerance, and negative nitrogen and calcium balance; (2) fluid and electrolyte disturbances such as sodium and fluid retention, hypertension, potassium loss, and hypokalaemic alkalosis; (3) musculo-skeletal effects (e.g., myopathy, abdominal distension, osteoporosis, aseptic necrosis of femoral and humeral heads); (4) gastro-intestinal effects including gastric and duodenal ulceration, perforation, and hemorrhage; (5) dermatological effects such as impaired wound healing, skin atrophy, striae, petechiae and ecchymoses, bruising, facial erythema, increased sweating, and acne; (6) central nervous system effects (e.g., psychic disturbances ranging from euphoria to frank psychotic manifestations, convulsions, pseudotumor cerebri (benign intracranial hypertension) with vomiting and papilioedema); (7) ophthalmic effects including glaucoma, increased intraocular pressure, posterior subcapsular cataracts; and (8) immunosuppressive effects such as increased susceptibility to infections, decreased responsiveness to vaccination and skin tests. Thus, unnecessary exposure to anti-cancer therapy (e.g., glucocorticoids, such as dexamethasone), should be limited to the extent possible to avoid causing complications and discomfort without significant positive benefits.

Figure 26:
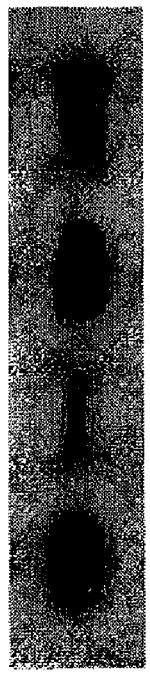
FIG. 26 shows that the effect of dexamethasone on the expression of GP88 mRNA in multiple myeloma (ARP-1) cells. Dexamethasone significantly inhibits the expression of GP88 mRNA in ARP-1 cells.
Figure 27A:
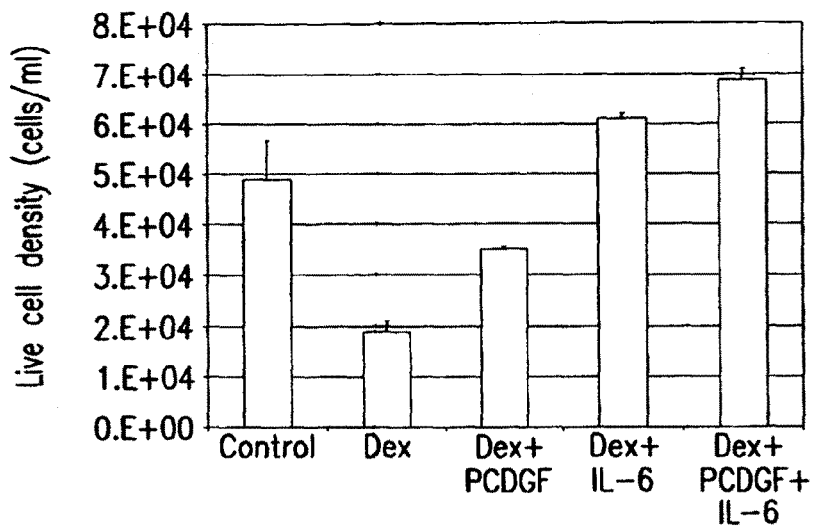
FIGS. 27A and 27B shows the effects of GP88 on the cell growth (27A) and viability (27B) of dexamethasone-treated ARP-1 cells. Dexamethasone decreases the cell growth and viability of ARP-1 cells. GP88 partially reverses the negative effects of dexamethasone on the cell growth and viability of ARP-1 cells.
Figure 27B:
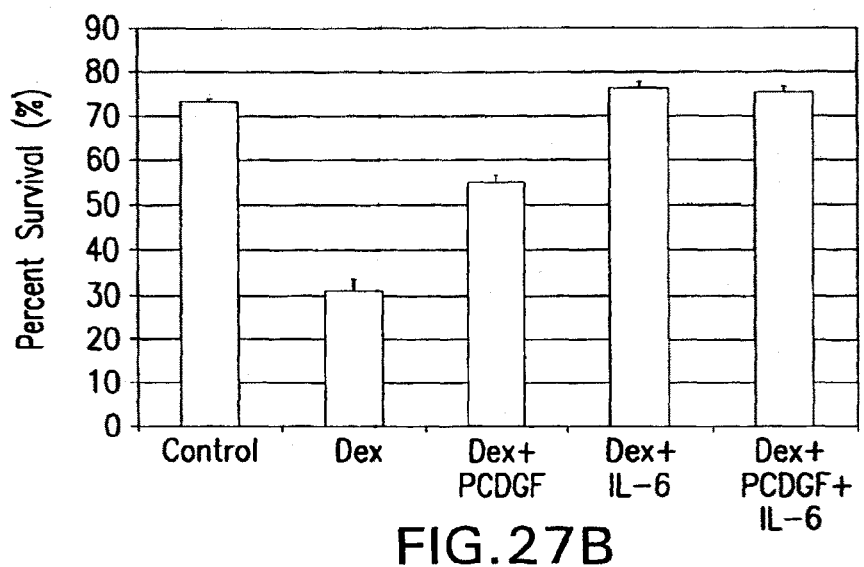
Figure 28:
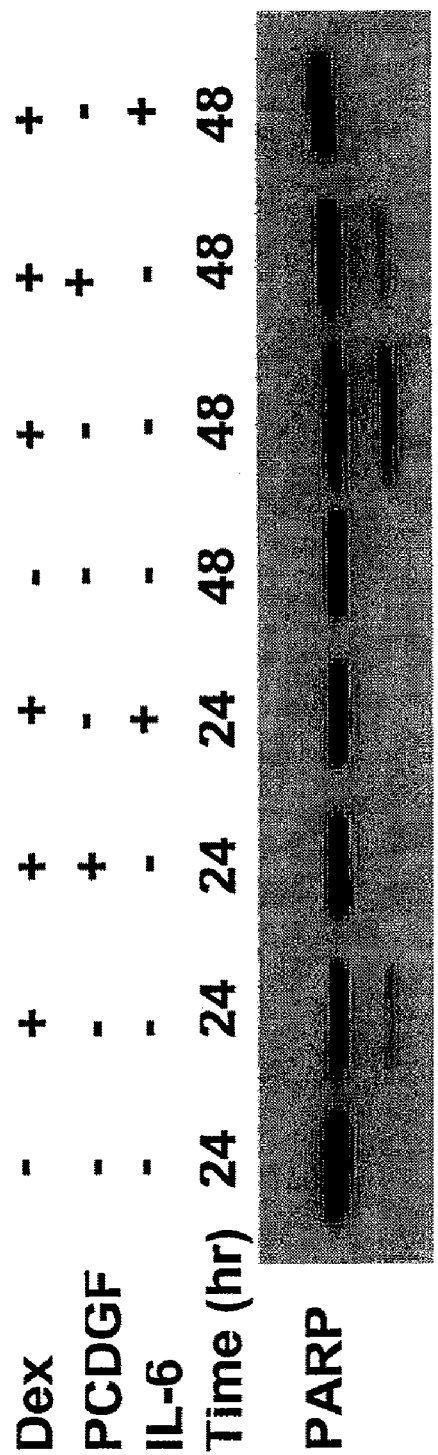
FIG. 28 shows the effect of GP88 on PARP cleavage in dexamethasone-treated ARP-1 cells. GP88 significantly reduces PARP cleavage at 24 and 48 hours following treatment with dexamethasone.

Dexamethasone induces apoptosis of multiple myeloma cells. As shown in FIG. 26, dexamethasone also inhibits GP88 protein expression. GP88 protein expression was measured by Western blot analysis of conditioned media collected by ARP-1 cell cultures in the presence and absence of dexamethasone alone and in combination with IL-6 (FIG. 26). Dexamethasone significantly inhibited the expression of GP88 protein. The addition of exogenous GP88 overcomes the apoptosis-inducing effects of dexamethasone (FIGS. 27A and 27B). As shown in FIGS. 27A and 27B, GP88 significantly increased both cell growth (FIG. 27A) and cell viability (FIG. 27B) of ARP-1 cells treated with dexamethasone. FIG. 28 shows that GP88 significantly reduces the cleavage of an apoptosis marker PARP (Poly (ADP-ribose) polymerase) in dexamethasone-treated ARP-1 cells. Cleavage of PARP into two fragments is a marker of cell apoptosis. Thus, GP88 has an anti-apoptotic effect and can inhibit dexamethasone-induced killing of B-cell leukemia cells.

Figure 29:
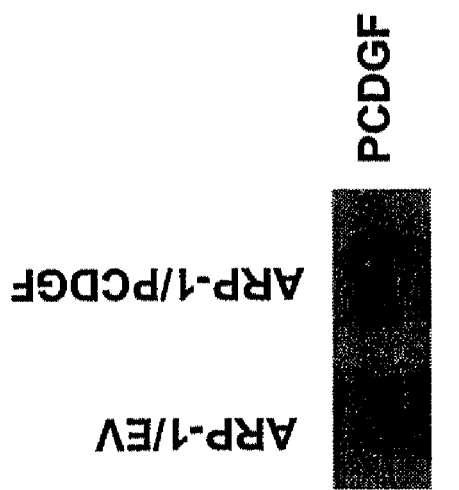
FIG. 29 shows GP88 protein expression in ARP-1 cells transfected with GP88 nucleic acid (lane 2) and an empty vector that does not contain GP88 nucleic acid (lane 1). GP88 is overexpressed in ARP-1 cells transfected with GP88 nucleic acid.
Figure 30A:
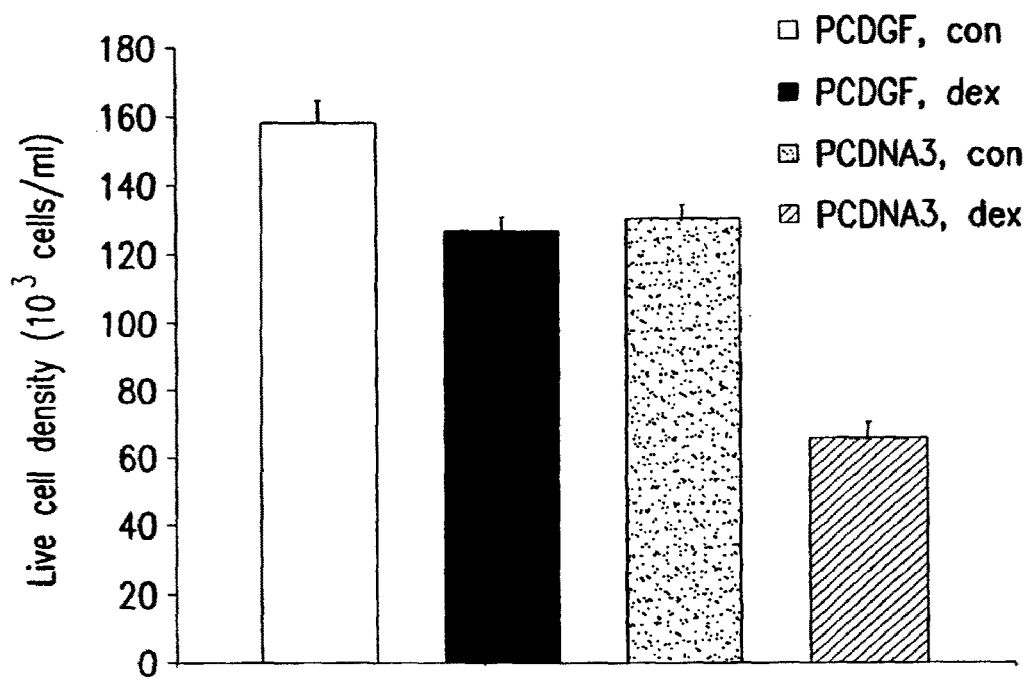
FIGS. 30A and 30B shows the effect of dexamethasone on the cell growth (30A) and viability (30B) of ARP-1 cells transfected with GP88 nucleic acid and ARP-1 cells transfected with an empty vector. The decrease in cell growth and viability of ARP-1 cells treated with dexamethasone is significantly reduced in cells transfected with GP88 nucleic acid.
Figure 30B:
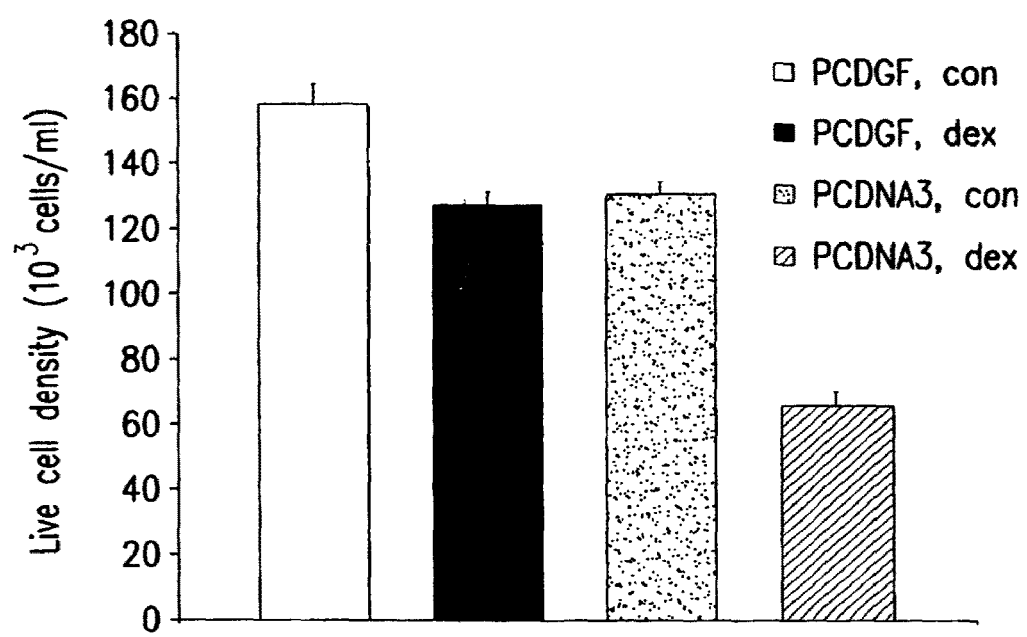

Increased levels of GP88 in MM cells are responsible for the transition of MM cells to a glucocorticoid resistant form. As shown in FIG. 29, cells transfected with GP88 (ARP-1/PCDGF) produced ten times more GP88 than untransfected cells or control ARP-1 cells that were transfected with empty vector (ARP-1/EV). (FIG. 29). MM cells transfected with GP88 show an increased growth rate and viability (resistance to the killing effect of dexamethasone) (FIGS. 30A and 30B). As shown in FIG. 30A, the ARP-1/PCDGF cells had a higher growth rate and were more resistant to the apoptotic effects of dexamethasone (columns 1 and 2) than the ARP-1/empty vector control cells (columns 3 and 4). Likewise, the ARP-1/PCDGF cells showed increased viability in response to the addition of dexamethasone (columns 1 and 2) that the ARP-1/empty vector cells. Thus, the presence of GP88 indicates that B-cells are or have become dexamethasone-resistant.

Methods of determining whether a patient is responding or responsive to anti-cancer therapy by detecting the presence of GP88 in a tissue sample containing B-cells are also provided by the invention. The term "responding" to anti-cancer therapy refers to patients who are receiving anti-cancer therapy. One embodiment of the invention will determine if such patients should continue to receive anti-cancer therapy. The term "responsive" to anti-cancer therapy refers to patients who are not yet receiving anti-cancer therapy. Another embodiment of the invention will determine if such patients should begin to receive anti-cancer therapy. Increased levels of GP88 in tissue samples (e.g., detectable increase in the level of GP88) containing B-cells over time indicate that the patient is not responding or responsive to anti-cancer therapy (e.g., glucocorticoids such as dexamethasone). Alternatively, increased-levels of GP88 in B-cells compared to normal or peripheral tissues is sufficient to indicate that the patient is not responding or responsive to glucocorticoid therapy. GP88 protein and/or nucleic acids (e.g., DNA or RNA encoding GP88) can be detected as described above (e.g., using anti-GP88 antibodies, antisense nucleic acids). In another embodiment, the GP88 level in an individual patient's B cells or tissues containing B-cells can be periodically monitored. An increased level of GP88 in a patient's B-cells or in tissues containing B-cells over time indicates that the patient is not responding or responsive to anti-cancer therapy.

Recombinant GP88

The present invention is also directed to DNA expression systems for expressing a recombinant GP88 polypeptide or a functional derivative thereof substantially free of other mammalian DNA sequences. Such DNA may be double or single stranded. The DNA sequence should preferably have about 20 or more nucleotides to allow hybridization to another polynucleotide. In order to achieve higher specificity of hybridization, characterized by the absence of hybridization to sequences other than those encoding the GP88 protein or a homologue or functional derivative thereof, a length of at least 50 nucleotides is preferred.

The present invention is also directed to the above DNA molecules, expressible vehicles or vectors as well as hosts transfected or transformed with the vehicles and capable of expressing the polypeptide. Such hosts may be prokaryotic, preferably bacteria, or eukaryotic, preferably yeast, mammalian or insect cells. A preferred vector system includes baculovirus expressed in insect cells. The DNA can be incorporated into host organisms by transformation, transduction, transfection, infection or related processes known in the art. In addition to DNA and mRNA sequences encoding the GP88 polypeptide, the invention also provides methods for expression of the nucleic acid sequence. Further, the genetic sequences and oligonucleotides allow identification and cloning of additional polypeptides having sequence homology to the polypeptide GP88 described here.

An expression vector is a vector which (due to the presence of appropriate transcriptional and/or translational control sequences) is capable of expressing a DNA (or cDNA) molecule which has been cloned into the vector and thereby produces a polypeptide or protein. Expression of the cloned sequence occurs when the expression vector is introduced into an appropriate host cell. If a prokaryotic expression vector is employed, then the appropriate host cell would be any prokaryotic cell capable of expressing the cloned sequence. Similarly, if an eukaryotic expression system is employed, then the appropriate host cell would be any eukaryotic cell capable of expressing the cloned sequence. Baculovirus vector, for example, can be used to clone GP88 cDNA and subsequently express the cDNA in insect cells.

A DNA sequence encoding GP88 polypeptide or its functional derivatives may be recombined with vector DNA in accordance with conventional techniques including blunt-ended or staggered ended termini for ligation, restriction enzyme digestion to provide appropriate termini, filling in cohesive ends as appropriate, alkaline phosphatase treatment to avoid undesirable joining, and ligation with proper enzyme ligases. Techniques for such manipulations are discussed in (35).

A nucleic acid molecule is capable of expressing a polypeptide if it contains nucleotide sequences which contain transcriptional and translational regulatory information and such sequences are operably linked to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism but shall in general include a promoter region, which in prokaryotes contains both the promoter (which directs the initiation of RNA transcription) as well as the DNA sequences which when transcribed into RNA will signal the initiation of protein synthesis. Such regions will normally include those 5' non-coding sequences involved with the initiation of transcription, translation such as the TATA box, capping sequence, CAAT sequence and the like.

If desired, the 3' non-coding region to the gene sequence encoding the protein may be obtained by described methods (screening appropriate cDNA library or PCR amplification). This region may be retained for the presence of transcriptional termination regulatory sequences such as termination and polyadenylation. Thus, by retaining the 3' region naturally contiguous to the DNA sequence coding for the protein, the transcriptional termination signals may be provided. Where the transcription termination signals are not provided or satisfactorily functional in the expression host cells, then a 3' region from another gene may be substituted.

Two DNA sequences such as a promoter region sequence and GP88 encoding sequence are said to be operably linked if the nature of the linkage between the sequences does not result in the introduction of a frame-shift mutation or interfere with the ability of the promoter sequence to direct transcription of the polypeptide gene sequence.

The promoter sequences may be prokaryotic, eukaryotic or viral. Suitable promoters are inducible, repressible or constitutive. Examples of suitable prokaryotic promoters are reviewed by.

Eukaryotic promoters include but are not limited to the promoter for the mouse methallothionein I gene, the TK promoter of Herpes Virus, the gene gal4 promoter, the SV40 early promoter, the mouse mammary tumor virus (MMTV) promoter, and the cytomegalovirus (CMV) promoter. Strong promoters are preferred. Examples of such promoters are those which recognize the T3, SP6 and T7 polymerases, the PL promoter of bacteriophage lambda, the recA promoter, the promoter of the mouse methallothionein I gene, the SV40 promoter and the CMV promoter.

It is to be understood that application of the teachings of the present invention to a specific problem or environment will be within the capability of one having ordinary skill in the art in light of the teachings contained herein. The present invention is more fully illustrated by the following non-limiting examples.

Example 1

Cell Lines and Reagents

Daudi, Raji, KOPM-28, ARP-1, RPMI 8226, Jurkat, KOPT-K1, and HL-60 were obtained from the American Type Culture Collection (ATCC, Manhassas, Va.). RPMI 1640 medium, FBS, and Trizol was obtained from Invitrogen life technologies (Carlsbad, Calif.). Alexa 456 conjugated goat anti mouse IgG F(ab')2 and Alexa 488 conjugated goat anti rabbit IgG F(ab')2 were obtained from Molecular Probes (Eugene, Oreg.). IL-6 was obtained from Upstate Biotechnology Inc. (Lack Placid, N.Y.). PD98059, anti phosph-MAPK antibody, anti phosph-Akt antibody, anti Akt antibody, anti phosph-tyr-STAT3 were obtained from New England Biolabs (Beverly, Mass.). Anti STAT3 was obtained from BD Biosciences. Anti MAPK antibody was obtained from Santa Cruz Biotechnology (Santa Cruze, Calif.). LY194002 was obtained from Biomol (Plymouth Meeting, Pa.). Supersignal Western chemiluminescent substrate was obtained from Pierce (Rockford, Ill.). Immobilon-P transfer membranes were obtained from Millipore (Bedford, Mass.). Monoclonal antibodies to anti human κ or λ light chains were obtained from Dako (Carpinteria, Calif.). Protein A sepharose was obtained from Amersham Pharmacia Biotech (Piscataway, N.J.). GP88 and anti-GP88 antibody were purified in our lab and are described in U.S. Pat. No. [insert]. All other reagents were obtained from Sigma.

GP88 Protein Expression

Daudi, Raji, KOPM-28, ARP-1, RPMI 8226, Jurkat, HL-60, and KOPT-K1 were cultured at a density of $1 \times 10^5$ cells/ml in RPMI medium supplemented with 10% FBS. Until the cells reach a density of $1 \times 10^6$ cells/ml, the culture media equivalent to $1.5 \times 10^7$ live cells were collected to measure GP88 protein expression. Immunoprecipitaion and Western Blot analysis were carried out as described previously (18) using 50 ug/ml anti-GP88 F(ab') conjugated to HRP as the detecting antibody.

Northern Blot Analysis

RPMI 8226 and ARP-1 cell were cultured in 10% FBS RPMI medium. RNA isolation was carried out using Trizol. Northern Blot analysis was carried out as described previously (18).

Cell Growth and Survival Assay

RPMI 8226 or ARP-1 cells were cultured in 10% FBS RPMI. Before the assay, cells were washed by serum free RPMI 1640 twice and cultured in serum free RPMI 1640 medium for 24 hours. GP88 or IL-6 was added to media at indicated concentration. Live cell density and viability were determined by trypan blue exclusion and cell counting. Experiments were carried out in triplicate sets with results expressed as mean±SD.

Anti-GP88 Neutralizing Assay

RPMI 8226 cells were cultured in 10% FBS RPMI 1640, washed by RPMI 1640 twice, and cultured in RPMI 1640 media at 1×10⁵ cells/ml. Affinity purified anti-GP88, non-immuno rabbit IgG, or affinity purified anti-GP88 antibody with GP88 was added as appropriate. After 48 hours, live cell density was checked by trypan blue staining and cell counting. Experiments were carried out in triplicate sets and the result was expressed as mean±SD.

MAPK Assay

ARP-1 cells were cultured in 10% FBS RPMI 1640 medium, washed by RPMI 1640 twice, and resuspended at $2.5 \times 10^5$ live cells/ml in RPMI 1640. After overnight starvation, ARP-1 cells were either treated with or without 30CM PD98059 for 60 min. GP88 was added to final concentration of 200 ng/ml except wells for negative controls. Ten milliliters of cell culture was used for each sample. After ten minutes of incubation, the cells were lysed by loading buffer. Cell lysates were separated on a 12.5% SDS-PAGE gel. The phosph-MAPK and total MAPK proteins were detected by anti-phoph-MAPK and anti MAPK antibodies respectively using Western blot analysis.

Akt Assay

ARP-1 cells were cultured in 10% FBS RPMI 1640 medium, washed in RPMI 1640 twice, and resuspended at $2.5 \times 10^5$ live cells/ml in RPMI 1640. After overnight starvation, ARP-1 cells were either treated with or without 50CM LY194002 for ten minutes. GP88 was added to the experimental wells on a microtiter plate at a final concentration of 200 ng/ml. GP88 was not added to control wells. Ten milliliters of cell culture was used for each sample. After ten minutes of incubation, cells were lysed by loading buffer. Cell lysates were separated on a 12.5% SDS-PAGE gel. The phosph-Akt and total Akt proteins were detected by anti-phoph-Akt and anti-Akt antibodies respectively using Western blot analysis.

STAT3 Assay

ARP-1 cells were cultured in 10% FBS RPMI 1640 medium, washed twice in RPMI 1640 medium, and resuspended at $2.5 \times 10^5$ live cells/ml in RPMI 1640. After starvation of the cell culture overnight, ARP-1 cells were treated with 200 ng/ml GP88 or 10 ng/ml IL-6 for 15 min. Cells were lysed by loading buffer and separated on a 7.5% SDS-PAGE. $3 \times 10^6$ cells were used for each sample. The phosph-tyr-STAT3 and total STAT3 proteins were detected by anti-phoph-tyr-STAT3 and anti STAT3 antibodies respectively using Western blot analysis.

Immunocytochemistry Studies

Bone marrow smears obtained from multiple myeloma patients at the University of Maryland Greenbaum Cancer Center were fixed for 15 minutes on ice with 2% paraformaldehyde in PBS, washed by PBS, and permeabilized with 0.2% Triton X100 for 15 minutes at room temperature. The slides were stained with 0.85 μg/ml rabbit anti-human GP88 antibody at room temperature for 1 hour, washed by PBS, and incubated with secondary 2 μg/ml Alexa 488-conjugated goat anti rabbit IgG F(ab')2 at room temperature for 1 hour. These slides were also stained with 0.25 μg/ml monoclonal antibodies to anti human K or X light chains at room temperature for 1 hour, washed by PBS, and followed by incubation with 1 μg/ml Alexa456 conjugated goat anti mouse IgG F(ab')2 at room temperature for 1 hour. Finally, samples were stained by 0.5 μg/ml DAPI at room temperature for 15 minutes. Stained bone marrow samples were observed with Olympus BX40 fluorescence microscope equipped with 100 W mercury lamp and appropriate filters.

GP88 Expression in Human Hematological Cell Line

We examined GP88 expression in several human leukemic cell lines. Samples examined were standardized to the same cell number. FIG. 16 shows GP88 protein expression was high in human B cell lines (Raji and Daudi) and human MM cell lines (ARP-1 and RPMI 8226). In contrast, no GP88 was produced in human T cell lines (Jurkat and KOPT-K1) and promyelocytic leukemia (HL-60). A low level of GP88 was found in macrophage cell line (KOPM-28). HL-60 is a promyelocytic cell line that can be induced to differentiate terminally to granulocyte-like cells or monocyte/macrophage-like cells upon exposure to different reagents (19). These results show that GP88 is preferentially expressed by hematological malignancies of B cell lineage. The level of GP88 mRNA expression in the MM cell lines ARP-1 and RPMI 8226 is shown in FIG. 17.

GP88 Function in Two Human MM Cell Lines: RPMI 8226 and ARP-1

The effect of exogenously added GP88 on the growth and survival of RPMI 8226 (FIG. 18) and ARP-1 (FIG. 19) was examined and compared to IL-6, a known paracrine growth stimulator of MM cell growth. As shown in FIG. 3A, RPMI 8226 cells were starved in RPMI medium only for 24 hours, then GP88 or IL-6 was added to medium. After 24 hour treatment 50 ng/ml ($5.7 \times 10^{-7}$ M), 100 ng/ml ($1.1 \times 10^{-6}$ M), 200 ng/ml ($2.3 \times 10^{-6}$ M) GP88, and 10 ng/ml ($4.5 \times 10^{-7}$ M) IL-6 stimulated the growth of RPMI 8226 cells by 1.3, 1.5, 1.5, and 1.6-fold, respectively. After 48 hour treatment, 50, 100, 200 ng/ml GP88, and 10 ng/ml IL-6 stimulated the growth of RPMI 8226 cells by 1.7, 2.5, 2.6, and 2.8 fold, respectively. These data show that GP88 stimulates the growth of RPMI 8226 cells in a dose and time dependent fashion similarly to IL-6. In addition to stimulating the growth of human MM cells, exogenous GP88 also stimulated cell survival of RPMI 8226 similarly to IL-6 (FIG. 18B).

Dex-sensitive ARP-1 cells exhibited similar growth and survival effects in response to GP88. As shown in FIG. 19A, ARP-1 cells were starved in serum-free medium for 24 hours, then GP88 or IL-6 was added to medium. At 24 hours of treatment, 200 ng/ml GP88 and 10 ng/ml IL-6 stimulated the growth of ARP-1 cells by 1.3 and 1.4 fold, respectively. After 48 hours of treatment, 200 ng/ml GP88 and 10 ng/ml IL-6 stimulated the growth of ARP-1 cells by 2.3 and 2.6 fold, respectively. Similarly exogenous GP88 also stimulated cell survival of ARP-1 (FIG. 19B).

Effect of Anti-GP88 Neutralizing Antibody on the Growth of RPMI 8226 Cells

In order to check whether GP88 produced and secreted by MM cells was required for cell growth, we examined the effect of anti-GP88 neutralizing antibody on the growth of RPMI 8226 cells. We have shown previously that this antibody was able to inhibit the proliferation of breast cancer cells overexpressing GP88 (20). As shown in FIG. 20, treatment of RPMI 8226 cell with 200 μg/ml affinity purified anti-GP88 antibody inhibited RPMI 8226 cell growth by about 50% in serum free condition. However, treatment of RPMI 8226 cells with 200 μg/ml non-immuno rabbit IgG did not significantly inhibit RPMI 8226 cell growth. Addition of exogenous 200 ng/ml GP88 prevented the inhibition effect of anti-GP88 antibody. These results show that GP88 stimulated MM cell growth in an autocrine fashion.

Signaling Pathway Stimulated by GP88 in ARP-1 Cells

Figure 21B:
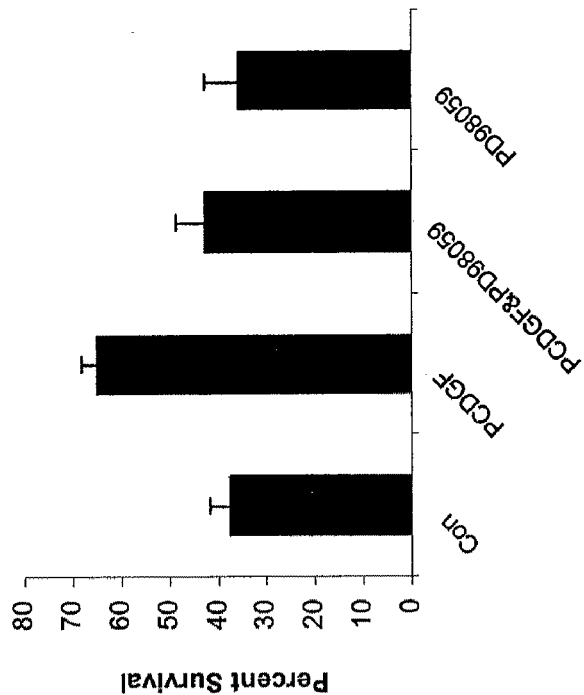
FIGS. 21A and 21B show the effect of GP88 and PD98059 (a MEK inhibitor) on cell growth and survival. GP88 increased both live cell density (FIG. 21A) and percent survival (FIG. 21B) in ARP-1 cells. These results show that GP88 activates the MAPK pathway in ARP-1 cells and that MAPK stimulates GP88-induced cell growth.
Figure 21A:
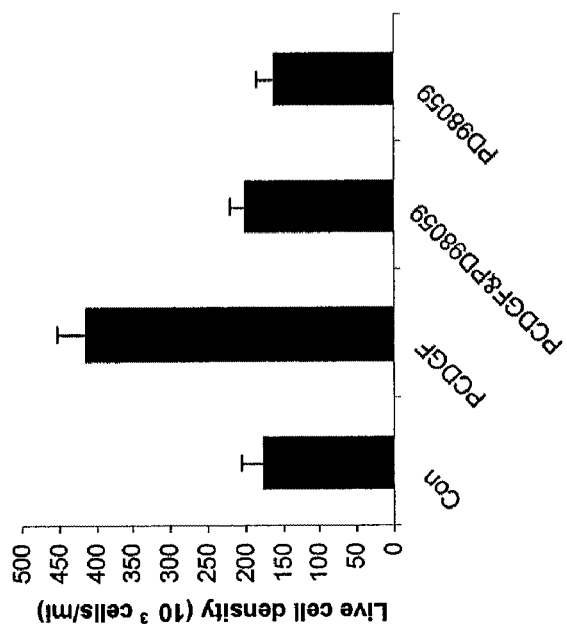
Figure 22:
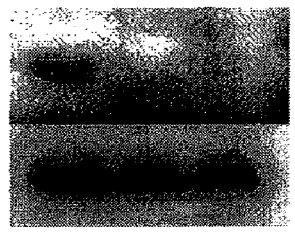
FIG. 22 shows that phosphorylation of Erk1 and Erk2 through the MAPK pathway is blocked by MEK inhibitor PD98059 in ARP-1 cells. These results show that GP88 activates the MAPK pathway in ARP-1 cells and that MAPK stimulates GP88-induced cell growth.
Figure 23:
FIG. 23 shows that GP88 stimulated phosphorylation of Akl in ARP-1 cells is blocked by PI3 K inhibitor LY294002. The results show that GP88 activates the PI3 kinase signal pathway in ARP-1 cells.

We examined signal pathways involved in growth factor signal transduction to determine their role, if any, in the GP88 signal transduction pathway in MM cells. MAPK signal pathway plays a key role in proliferation process and MAPK activity is stimulated in response to many different growth factors (21,22). PI3K signal pathway is primarily associated with survival and cell growth regulation (23, 24). FIG. 21 shows that stimulation of ARP-1 cell growth and survival by 200 ng/ml of GP88 was blocked by the MEK inhibitor PD98059 at 30 μM. FIG. 22 shows 200 ng/ml GP88 activated the phosphorylation of Erk1 and Erk2 and this phosphorylation was also inhibited by 30 μM PD98059. Together, these results show that GP88 activated MAPK signal pathway in ARP-1 cells and that MAPK was responsible for stimulation of cell growth by GP88. To determine the role of the PI3K signal pathway, we assessed the phosphorylation of Akt. Akt contains an amino-terminal pleckstrin homology (PH) domain that binds phosphorylated lipids at the membrane in response to activation of PI3 kinase (25, 26). FIG. 23 shows that GP88 stimulates the phosphorylation of Akt in ARP-1 cells and this phosphorylation was inhibited by PI3 K inhibitor LY294002 at 50 μM. These results showed that GP88 activated PI3 kinase signal pathway in ARP-1 cells.

Figure 24:
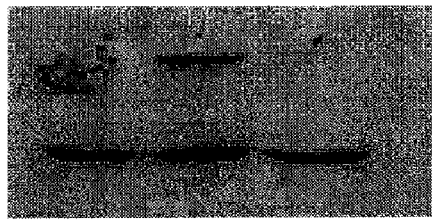
FIG. 24 shows that GP88 does not induce phosphorylation of STAT3. The results show that GP88 does not activate the JAK/STAT3 signal pathway in human multiple myeloma cells.

MAPK and JAK/STAT pathways are two important signaling pathways in human MM cells induced by IL-6 (6). In order to check whether GP88 activates JAK/STAT pathways in human MM cells, the phosphorylation of STAT3 was assessed following stimulation of MM cells by 200 ng/ml GP88 or 10 ng/ml IL-6. As shown in FIG. 24, only IL-6, but not GP88, stimulates the phosphorylation of STAT3. These data suggest that GP88 does not activate the JAK/STAT3 pathway in human MM cells.

Immunocytochemistry Studies of Human Patient Bone Marrow Smears

We examined GP88 expression in 13 bone marrow biopsy samples from patients with multiple myeloma by immunocytochemistry staining of GP88 and human κ/λ light chains. The presence κ or λ light chains in bone marrow cells is a marker of myeloma cells (27). Table 1 demonstrates that GP88 was overexpressed in bone marrow smears of MM patients. Staining of the samples with anti-human κ or λ light chains showed that the myeloma cells that stained positive for GP88 were positive for κ or λ light chains indicating that the cells that overexpress GP88 in bone marrow smears of MM patients are the multiple myeloma cells. GP88-positive cells were not observed in the bone marrow smears from patients in remission (patients 2, 5a, 6 and 9) where κ or λ light chain-positive cells were not detected. It is important to note that when the relapse of MM disease occurred in patient 5a, GP88 expression was detected in the bone marrow samples and co-localized with cells expressing K light chains (5b in Table 1). The κ/λ chain positive cells showed 100% GP88 positive staining by counting 100 κ/λ chain positive cells. A typical triple staining by DAPI, κ/λ chain, and GP88 is shown in FIG. 25. These data clearly indicated that GP88 expression is associated with myeloma cells from all MM patients examined and correlated well with the presence of the disease.

The Effects of Dexamethasone (Dex) and IL-6 Effect on GP88 Protein Expression in ARP-1 Cells ARP-1 cells were seeded in 10% CT-FBS RPMI 1640 in the presence of $10^{-7}$ M Dex or 10 ng/ml IL-6 added alone or in combination. Control cells were cultivated with vehicle medium that did not contain Dex or IL-6. After 48 hours, the cell culture medium was changed to RPMI 1640 for 24 hours and the conditioned medium was collected. The GP88 secreted in the conditioned medium was measured by immunoprecipitation and western blot analysis (FIG. 26). Dex inhibited the expression of GP88 in Dex-treated ARP-1 cells.

The Effects of Exogenous Addition of GP88 and IL-6 on Dex-induced Cell Death

ARP-1 cells were cultured in media containing 10% CT-FBS RPMI 1640 medium in the presence of $10^{-7}$ M Dex, 200 ng/ml GP88, or 10 ng/ml IL-6 added alone or in combination. After 48 hours, the live cell density and cell viability were checked by trypan blue exclusion and counting with a hemocytometer. FIG. 27A shows the effect on live cell density and FIG. 27B shows the effect on cell viability. GP88 increased the growth and viability of Dex-treated ARP-1 cells.

The Effects of GP88 on PARP Cleavage in ARP-1 Cells

ARP-1 cells were seeded and treated with $10^{-7}$ M Dex, 200 ng/ml PCDGF, and 10 ng/ml IL-6 as described above. Cells were collected at 24 hours and 48 hours. ARP-1 cells were lysed and 100 μg protein per lane were used to analyze PARP cleavage by SDS-PAGE and western blot analysis. GP88 inhibited the apoptotic effects of Dex on Dex-treated ARP-1 cells (FIG. 28).

Overexpression of GP88 in ARP-1 Cells

Dexamethasone-sensitive human MM cell line ARP-1 was transfected with expression vector pcDNA3 containing a CMV promoter, a neomycin resistant gene, and GP88 cDNA by electroporation. Transfected cells were selected in the presence of G418. GP88 expression in the cell culture media was detected by immunoprecipitation and western blot analysis. As shown in FIG. 29, ARP-1 cells transfected with GP88 (ARP-1/PCDGF) had elevated levels of GP88 compared to cells transfected with an empty expression vector (ARP-1/EV).

The Effects of Dex on ARP-1 and GP88 Overexpressed ARP-1 Cells

ARP-1/PCDGF cells that overexpress GP88 and ARP-1/EV were cultured in 10% CT-FBS RPMI with or without $10^{-7}$ M Dex. Cell density (A) and viability (B) were measured after 24 hours. As shown in FIGS. 30A and 30B, Dex-induced reduction in cell growth and viability was significantly reduced in cells with elevated levels of GP88 (columns 1 and 2) compared to cells that did not express GP88 (columns 3 and 4).

The Effects of GP88 Over Expression Dex-Induced PARP Cleavage

Figure 31:
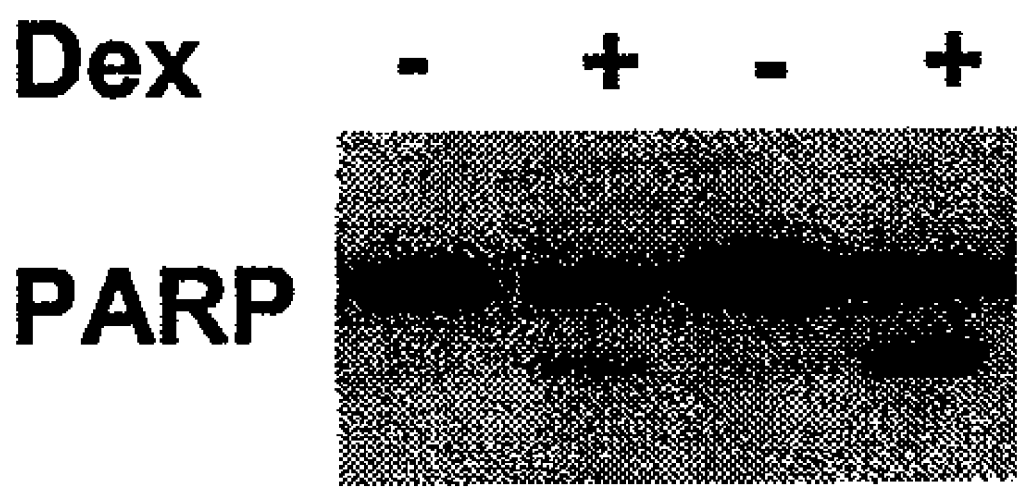
FIG. 31 shows the effect of dexamethasone on PARP cleavage in ARP-1 cells overexpressing GP88. ARP-1 cells overexpressing GP88 have significantly reduced levels of PARP cleavage.

Empty vector control and PCDGF overexpressing ARP-1 cells were treated with or without $10^{-7}$ M Dex. After 48 hours, the cells were lysed to measure the expression of intact and cleaved PARP (FIG. 31). Cells overexpressing GP88 (ARP-1/PCDGF) showed greatly reduced cleavage of PARP compared to cells that did not express GP88. Thus, GP88 inhibits the apoptotic effects of dexamethasone on ARP-1 cells.

REFERENCES

1. Niesvizky, R, D. Siegel, and J. Michaeli. 1993. Biology and treatment of multiple myeloma. Blood Reviews 7, no. 1:24.
2. Hallek, M., P. L. Bergsagel, and K. C. Anderson. 1998. Multiple myeloma: increasing evidence for a multistep transformation process. Blood 91, no. 1:3.
3. Hawley, R. G., and L. C. Berger. 1998. Growth control mechanisms in multiple myeloma. Leukemia & Lymphoma 29, no. 5-6:465.
4. Oken, M. M. 1997. Multiple myeloma: prognosis and standard treatment. Cancer Investigation 15, no. 1:57.
5. Alexanian, R., and M. Dimopoulos. 1994. The treatment of multiple myeloma. New England Journal of Medicine 330, no. 7:484.
6. Jelinek, D. F. 1999. Mechanisms of myeloma cell growth control. Hematology—Oncology Clinics of North America 13, no. 6:1145.
7. Georgii-Hemming, P., H. J. Wikiund, O. Ljunggren, and K Nilsson. 1996. Insulin-like growth factor I is a growth and survival factor in human multiple myeloma cell lines. Blood 88, no. 6:2250.
8. Freund, G. G., D. T. Kulas, and R. A. Mooney. 1993. Insulin and IGF-1 increase mitogenesis and glucose metabolism in the multiple myeloma cell line, RPMI 8226. Journal of Immunology 151, no. 4:1811.
9. Jelinek, D. F., T. E. Witzig, and B. K. Arendt. 1997. A role for insulin-like growth factor in the regulation of IL-6-responsive human myeloma cell line growth. Journal of Immunology 159, no. 1:487.
10. Ge, N. L., and S. Rudikoff. 2000. Insulin-like growth factor I is a dual effector of multiple myeloma cell growth. Blood 96, no. 8:2856.
11. Greipp, P. K, and T. Witzig. 1996. Biology and treatment of myeloma. Curr Opin Oncol 8, no. 1:20.
12. Zhou, J., G. Gao, J. W. Crabb, and G. Serrero. 1993. Purification of an autocrine growth factor homologous with mouse epithelin precursor from a highly tumorigenic cell line. Journal of Biological Chemistry 268, no. 15:10863.
13. Zhang, H., and G. Serrero. 1998. Inhibition of tumorigenicity of the teratoma PC cell line by transfection with antisense cDNA for PC cell-derived growth factor (PCDGF, epithelin/granulin precursor). Proceedings of the National Academy of Sciences of the United States of America 95, no. 24:14202.
14. Lu, R., and G. Serrero. 2000. Inhibition of PC cell-derived growth factor (PCDGF, epithelin/granulin precursor) expression by antisense PCDGF cDNA transfection inhibits tumotigenicity of the human breast carcinoma cell line MDA-MB-468. Proceedings of the National Academy of Sciences of the United States of America 97, no. 8:3993.
15. Plowman, G. D., J. M. Green, M. G. Neubauer, S. D. Buckley, V. L. McDonald, G. J. Todaro, and M. Shoyab. 1992. The epithelin precursor encodes two proteins with opposing activities on epithelial cell growth. Journal of Biological Chemistry 267, no. 18:13073.
16. Bhandari, V., R, P, G. Palfree, and A. Bateman. 1992. Isolation and sequence of the granulin precursor cDNA from human bone marrow reveals tandem cysteine-rich granulin domains. Proceedings of the National Academy of Sciences of the United States of America 89, no. 5:1715.
17. Xu, S. Q., D. Tang, S. Chamberlain, G. Pronk, F. R Masiarz, S. Kaur, M. Prisco, T. Zanocco-Marani, and R Baserga. 1998. The granulin/epithelin precursor abrogates the requirement for the insulin-like growth factor 1 receptor for growth in vitro. Journal of Biological Chemistry 273, no. 32:20078.
18. Lu, R., and G. Serrero. 1999. Stimulation of PC cell-derived growth factor (epithelin/granulin precursor) expression by estradiol in human breast cancer cells. Biochemical & Biophysical Research Communications 256, no. 1:204.
19. Birnie, G. D. 1988. The HL60 cell line: a model system for studying human myeloid cell differentiation. British Journal of Cancer—Supplement 9:41.
20. Lu, K, and G. Serrero. 2001. Mediation of estrogen mitogenic effect in human breast cancer MCF-7 cells by PC-cell-derived growth factor (PCDGF/granulin precursor). Proceedings of the National Academy of Sciences of the United States of America 98, no. 1:142.
21. Marshall, C. J. 1995. Specificity of receptor tyrosine kinase signaling: transient versus sustained extracellular signal-regulated kinase activation. Cell 80, no. 2:179.
22. Hunter, T. 1995. Protein kinases and phosphatases: the yin and yang of protein phosphorylation and signaling. Cell 80, no. 2:225.
23. Rodriguez-Viciana, P., P. H. Warne, A. Khwaja, B. M. Marte, D. Pappin, P. Das, M. D. Waterfield, A. Ridley, and J. Downward. 1997. Role of phosphoinositide 3-OH kinase in cell transformation and control of the actin cytoskeleton by Ras. Cell 89, no. 3:457.
24. Cantrell, D. A. 2001. Phosphoinositide 3-kinase signalling pathways. Journal of Cell Science 114, no. Pt 8:1439.
25. Franke, T. F., S. I. Yang, T. O. Chan, K. Datta, A. Kazlauskas, D. K. Morrison, D. K Kaplan, and P. N. Tsichlis. 1995. The protein kinase encoded by the Akt proto-oncogene is a target of the PDGF-activated phosphatidylinositol 3-kinase. Cell 81, no. 5:727.
26. Franke, T. F., D. R. Kaplan, and L. C. Cantley. 1997. PI3K: downstream AKTion blocks apoptosis. Cell 88, no. 4:435.
27. Hitzman, J. L., C. Y. Li, and P A. Kyle. 1981. Immunoperoxidase staining of bone marrow sections. Cancer 48, no. 11:2438.
28. Michaeli, J., C. G. Choy, and X. Zhang. 1997. The biological features of multiple myeloma. Cancer Investigation 15, no. 1:76.
29. Collins, S. J., R. C. Gallo, and R. E. Gallagher. 1977. Continuous growth and differentiation of human myeloid leukaemic cells in suspension culture. Nature 270, no. 5635:347.
30. Collins, S. J. 1987. The HL-60 promyelocytic leukemia cell line: proliferation, differentiation, and cellular oncogene expression. Blood 70, no. 5:1233.
31. Ferlin, M., N. Noraz, C. Hertogh, J. Brochier, N. Taylor, and B. Klein. 2000. Insulin-like growth factor induces the survival and proliferation of myeloma cells through an interleukin-6-independent transduction pathway. British Journal of Haematology 111, no. 2:626.
32. Seidel, C., A. Sundan, M. Hjorth, I. Turesson, I. M. Dahl, N. Abildgaard, A. Waage, and M. Borset. 2000. Serum syndecan-1: a new independent prognostic marker in multiple myeloma. Blood 95, no. 2:388.
33. Schaar, C. G., U. Kaiser, S. Snijder, F. Ong, J. Hermans, P. F. Franck, and J. C. Kluin-Nelemans. 1999. Serum interleukin-6 has no discriminatory role in paraproteinaemia nor a prognostic role in multiple myeloma. British Journal of Haematology 107, no. 1:132.

I claim:

1. A method of inhibiting the growth or viability of hematopoietic malignant cells comprising contacting hematopoietic malignant cells with a GP88 antagonist wherein said antagonist is an anti-GP88 antibody and inhibits the growth or viability of said hematopoietic malignant cells.

2. The method of claim 1, wherein said hematopoietic malignant cells are leukemia cells of B cell lineage.

3. The method of claim 1, wherein said hematopoietic malignant cells are multiple myeloma cells.

4. The method of claim 1, wherein said GP88 antagonist is a humanized anti-GP88 antibody.

5. The method of claim 1, wherein said GP88 antagonist is a neutralizing anti-GP88 antibody.

6. The method of claim 1, wherein said GP88 antagonist is a chimeric anti-GP88 antibody, wherein at least one portion is derived from a human.

* * * * *

SEQUENCE LISTING

<160> NUMBER OF SEQ ID NOS: 17

<210> SEQ ID NO 1
<211> LENGTH: 2137
<212> TYPE: DNA
<213> ORGANISM: Mus musculus

<400> SEQUENCE: 1

```
cggaccccga cgcagacaga cc atg tgg gtc ctg atg agc tgg ctg gcc ttc         52
                         Met Trp Val Leu Met Ser Trp Leu Ala Phe
                         1               5                   10 gcg gca ggg ctg gta gcc gga aca cag tgt cca gat ggg cag ttc tgc         100
Ala Ala Gly Leu Val Ala Gly Thr Gln Cys Pro Asp Gly Gln Phe Cys
                15                  20                  25 cct gtt gcc tgc tgc ctt gac cag gga gga gcc aac tac agc tgc tgt         148
Pro Val Ala Cys Cys Leu Asp Gln Gly Gly Ala Asn Tyr Ser Cys Cys
            30                  35                  40 aac cct ctt ctg gac aca tgg cct aga ata acg agc cat cat cta gat         196
Asn Pro Leu Leu Asp Thr Trp Pro Arg Ile Thr Ser His His Leu Asp
        45                  50                  55 ggc tcc tgc cag acc cat ggc cac tgt cct gct ggc tat tct tgt ctt         244
Gly Ser Cys Gln Thr His Gly His Cys Pro Ala Gly Tyr Ser Cys Leu
    60                  65                  70 ctc act gtg tct ggg act tcc agc tgc tgc ccg ttc tct aag ggt gtg         292
Leu Thr Val Ser Gly Thr Ser Ser Cys Cys Pro Phe Ser Lys Gly Val
75                  80                  85                  90 tct tgt ggt gat ggc tac cac tgc tgc ccc cag ggc ttc cac tgt agt         340
Ser Cys Gly Asp Gly Tyr His Cys Cys Pro Gln Gly Phe His Cys Ser
                95                  100                 105 gca gat ggg aaa tcc tgc ttc cag atg tca gat aac ccc ttg ggt gct         388
Ala Asp Gly Lys Ser Cys Phe Gln Met Ser Asp Asn Pro Leu Gly Ala
            110                 115                 120 gtc cag tgt cct ggg agc cag ttt gaa tgt cct gac tct gcc acc tgc         436
Val Gln Cys Pro Gly Ser Gln Phe Glu Cys Pro Asp Ser Ala Thr Cys
        125                 130                 135 tgc att atg gtt gat ggt tcg tgg gga tgt tgt ccc atg ccc cag gcc         484
Cys Ile Met Val Asp Gly Ser Trp Gly Cys Cys Pro Met Pro Gln Ala
    140                 145                 150 tct tgc tgt gaa gac aga gtg cat tgc tgt ccc cat ggg gcc tcc tgt         532
Ser Cys Cys Glu Asp Arg Val His Cys Cys Pro His Gly Ala Ser Cys
155                 160                 165                 170 gac ctg gtt cac aca cga tgc gtt tca ccc acg ggc acc cac acc cta         580
Asp Leu Val His Thr Arg Cys Val Ser Pro Thr Gly Thr His Thr Leu
                175                 180                 185 cta aag aag ttc cct gca caa aag acc aac agc gca gtg tct ttg cct         628
Leu Lys Lys Phe Pro Ala Gln Lys Thr Asn Ser Ala Val Ser Leu Pro
            190                 195                 200 ttt tct gtc gtg tgc cct gat gct aag acc cag tgt ccc gat gat tct         676
Phe Ser Val Val Cys Pro Asp Ala Lys Thr Gln Cys Pro Asp Asp Ser
        205                 210                 215 acc tgc tgt gag cta ccc act ggg aag tat ggc tgt tgt cca atg ccc         724
Thr Cys Cys Glu Leu Pro Thr Gly Lys Tyr Gly Cys Cys Pro Met Pro
    220                 225                 230 aat gcc atc tgc tgt tcc gac cac ctg cac tgc tgc ccc cag gac act         772
Asn Ala Ile Cys Cys Ser Asp His Leu His Cys Cys Pro Gln Asp Thr
235                 240                 245                 250 gta tgt gac ctg atc cag agt aag tgc cta tcc aag aac tac acc acg         820
Val Cys Asp Leu Ile Gln Ser Lys Cys Leu Ser Lys Asn Tyr Thr Thr
                255                 260                 265
```

```
gat ctc ctg acc aag ctg cct gga tac cca gtg aag gag gtg aag tgc          868
Asp Leu Leu Thr Lys Leu Pro Gly Tyr Pro Val Lys Glu Val Lys Cys
        270             275             280 gac atg gag gtg agc tgc cct gaa gga tat acc tgc cgc ctc aac              916
Asp Met Glu Val Ser Cys Pro Glu Gly Tyr Thr Cys Arg Leu Asn
    285             290             295 act ggg gcc tgg ggc tgc tgt cca ttt gcc aag gcc gtg tgt tgt gac          964
Thr Gly Ala Trp Gly Cys Cys Pro Phe Ala Lys Ala Val Cys Cys Asp
300             305             310 gat cac att cat tgc tgc ccg gca ggg ttt cag tgt cac aca gag aaa         1012
Asp His Ile His Cys Cys Pro Ala Gly Phe Gln Cys His Thr Glu Lys
315             320             325             330 gga acc tgc gaa atg ggt atc ctc caa gta ggg tgg atg aag aag gtc         1060
Gly Thr Cys Glu Met Gly Ile Leu Gln Val Gly Trp Met Lys Lys Val
                335             340             345 ata gcc ccc ctc cgc ctg cca gac cca cag atc ttg aag agt gat aca         1108
Ile Ala Pro Leu Arg Leu Pro Asp Pro Gln Ile Leu Lys Ser Asp Thr
        350             355             360 cct tgt gat gac ttc act agg tgt cct aca aac aat acc tgc tgc aaa         1156
Pro Cys Asp Asp Phe Thr Arg Cys Pro Thr Asn Asn Thr Cys Cys Lys
        365             370             375 ctc aat tct ggg gac tgg ggc tgc tgt ccc atc cca gag gct gtc tgc         1204
Leu Asn Ser Gly Asp Trp Gly Cys Cys Pro Ile Pro Glu Ala Val Cys
380             385             390 tgc tca gac aac cag cat tgc tgc cct cag ggc ttc aca tgt ctg gct         1252
Cys Ser Asp Asn Gln His Cys Cys Pro Gln Gly Phe Thr Cys Leu Ala
395             400             405             410 cag ggg tac tgt cag aag gga gac aca atg gtg gct ggc ctg gag aag         1300
Gln Gly Tyr Cys Gln Lys Gly Asp Thr Met Val Ala Gly Leu Glu Lys
            415             420             425 ata cct gcc cgc cag aca acc ccg ctc caa att gga gat atc ggt tgt         1348
Ile Pro Ala Arg Gln Thr Thr Pro Leu Gln Ile Gly Asp Ile Gly Cys
        430             435             440 gac cag cat acc agc tgc cca gta ggg caa acc tgc tgc cca agc ctc         1396
Asp Gln His Thr Ser Cys Pro Val Gly Gln Thr Cys Cys Pro Ser Leu
            445             450             455 aag gga agt tgg gcc tgc tgc cag ctg ccc cat gct gtg tgc tgt gag         1444
Lys Gly Ser Trp Ala Cys Cys Gln Leu Pro His Ala Val Cys Cys Glu
460             465             470 gac cgg cag cac tgt tgc ccg gcc ggg tac acc tgc aac gtg aag gcg         1492
Asp Arg Gln His Cys Cys Pro Ala Gly Tyr Thr Cys Asn Val Lys Ala
475             480             485             490 agg acc tgt gag aag gat gtc gat ttt atc cag cct ccc gtg ctc ctg         1540
Arg Thr Cys Glu Lys Asp Val Asp Phe Ile Gln Pro Pro Val Leu Leu
            495             500             505 acc ctc ggc cct aag gtt ggg aat gtg gag tgt gga gaa ggg cat ttc         1588
Thr Leu Gly Pro Lys Val Gly Asn Val Glu Cys Gly Glu Gly His Phe
        510             515             520 tgc cat gat aac cag acc tgt tgt aaa gac agt gca gga gtc tgg gcc         1636
Cys His Asp Asn Gln Thr Cys Cys Lys Asp Ser Ala Gly Val Trp Ala
        525             530             535 tgc tgt ccc tac cta aag ggt gtc tgc tgt aga gat gga cgt cac tgt         1684
Cys Cys Pro Tyr Leu Lys Gly Val Cys Cys Arg Asp Gly Arg His Cys
540             545             550 tgc ccc ggt ggc ttc cac tgt tca gcc agg gga acc aag tgt ttg cga         1732
Cys Pro Gly Gly Phe His Cys Ser Ala Arg Gly Thr Lys Cys Leu Arg
555             560             565             570 aag aag att cct cgc tgg gac atg ttt ttg agg gat ccg gtc cca aga         1780
Lys Lys Ile Pro Arg Trp Asp Met Phe Leu Arg Asp Pro Val Pro Arg
            575             580             585
```

```
ccg cta ctg taaggaaggg ctacagactt aaggaactcc acagtcctgg         1829
Pro Leu Leu gaaccctgtt ccgagggtac ccactactca ggcctcccta gcgcctcctc ccctaacgtc  1889
tccccggcct actcatcctg agtcacccta tcaccatggg aggtggagcc tcaaactaaa  1949
accttctttt atggaaagaa ggctctggcc aaaagccccg tatcaaactg ccatttcttc  2009
cggtttctgt ggaccttgtg gccaggtgct cttcccgagc acaggtgtt ctgtgagctt  2069 gcttgtgtgt gtgtgcgcgt gtgcgtgtgt tgctccaata aagtttgtac gctttctgaa  2129
aaaaaaaa                                                           2137

<210> SEQ ID NO 2
<211> LENGTH: 589
<212> TYPE: PRT
<213> ORGANISM: Mus musculus

<400> SEQUENCE: 2

Met Trp Val Leu Met Ser Trp Leu Ala Phe Ala Ala Gly Leu Val Ala
1               5                   10                  15

Gly Thr Gln Cys Pro Asp Gly Gln Phe Cys Pro Val Ala Cys Cys Leu
            20                  25                  30

Asp Gln Gly Gly Ala Asn Tyr Ser Cys Cys Asn Pro Leu Leu Asp Thr
        35                  40                  45

Trp Pro Arg Ile Thr Ser His Leu Asp Gly Ser Cys Gln Thr His
    50                  55                  60

Gly His Cys Pro Ala Gly Tyr Ser Cys Leu Leu Thr Val Ser Gly Thr
65                  70                  75                  80

Ser Ser Cys Cys Pro Phe Ser Lys Gly Val Ser Cys Gly Asp Gly Tyr
                85                  90                  95

His Cys Cys Pro Gln Gly Phe His Cys Ser Ala Asp Gly Lys Ser Cys
            100                 105                 110

Phe Gln Met Ser Asp Asn Pro Leu Gly Ala Val Gln Cys Pro Gly Ser
        115                 120                 125

Gln Phe Glu Cys Pro Asp Ser Ala Thr Cys Cys Ile Met Val Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Val Ser Pro Thr Gly Thr His Thr Leu Leu Lys Lys Phe Pro Ala
            180                 185                 190

Gln Lys Thr Asn Ser Ala Val Ser Leu Pro Phe Ser Val Val Cys Pro
        195                 200                 205

Asp Ala Lys Thr Gln Cys Pro Asp Asp Ser Thr Cys Cys Glu Leu Pro
    210                 215                 220

Thr Gly Lys Tyr Gly Cys Cys Pro Met Pro Asn Ala Ile Cys Cys Ser
225                 230                 235                 240

Asp His Leu His Cys Cys Pro Gln Asp Thr Val Cys Asp Leu Ile Gln
                245                 250                 255

Ser Lys Cys Leu Ser Lys Asn Tyr Thr Thr Asp Leu Leu Thr Lys Leu
            260                 265                 270

Pro Gly Tyr Pro Val Lys Glu Val Lys Cys Asp Met Glu Val Ser Cys
        275                 280                 285

Pro Glu Gly Tyr Thr Cys Cys Arg Leu Asn Thr Gly Ala Trp Gly Cys
    290                 295                 300
```

-continued

```
Cys Pro Phe Ala Lys Ala Val Cys Cys Asp Asp His Ile His Cys Cys
305                 310                 315                 320

Pro Ala Gly Phe Gln Cys His Thr Glu Lys Gly Thr Cys Glu Met Gly
                325                 330                 335

Ile Leu Gln Val Gly Trp Met Lys Lys Val Ile Ala Pro Leu Arg Leu
            340                 345                 350

Pro Asp Pro Gln Ile Leu Lys Ser Asp Thr Pro Cys Asp Asp Phe Thr
        355                 360                 365

Arg Cys Pro Thr Asn Asn Thr Cys Cys Lys Leu Asn Ser Gly Asp Trp
    370                 375                 380

Gly Cys Cys Pro Ile Pro Glu Ala Val Cys Cys Ser Asn Asn Gln His
385                 390                 395                 400

Cys Cys Pro Gln Gly Phe Thr Cys Leu Ala Gln Gly Tyr Cys Gln Lys
                405                 410                 415

Gly Asp Thr Met Val Ala Gly Leu Glu Lys Ile Pro Ala Arg Gln Thr
                420                 425                 430

Thr Pro Leu Gln Ile Gly Asp Ile Gly Cys Asp Gln His Thr Ser Cys
            435                 440                 445

Pro Val Gly Gln Thr Cys Cys Pro Ser Leu Gly Gly Ser Trp Ala Cys
450                 455                 460

Cys Gln Leu Pro His Ala Val Cys Cys Glu Asp Arg Gln His Cys Cys
465                 470                 475                 480

Pro Ala Gly Tyr Thr Cys Asn Val Lys Ala Arg Thr Cys Glu Lys Asp
                485                 490                 495

Val Asp Phe Ile Gln Pro Pro Val Leu Leu Thr Leu Gly Pro Lys Val
                500                 505                 510

Gly Asn Val Glu Cys Gly Glu Gly His Phe Cys His Asp Asn Gln Thr
            515                 520                 525

Cys Cys Lys Asp Ser Ala Gly Val Trp Ala Cys Cys Pro Tyr Leu Lys
    530                 535                 540

Gly Val Cys Cys Arg Asp Gly Arg His Cys Cys Pro Gly Gly Phe His
545                 550                 555                 560

Cys Ser Ala Arg Gly Thr Lys Cys Leu Arg Lys Ile Pro Arg Trp
                565                 570                 575

Asp Met Phe Leu Arg Asp Pro Val Pro Arg Pro Leu Leu
                580                 585
```

```
<210> SEQ ID NO 3
<211> LENGTH: 19
<212> TYPE: PRT
<213> ORGANISM: Artificial Sequence
<220> FEATURE:
<223> OTHER INFORMATION: synthetic peptide

<400> SEQUENCE: 3

Lys Lys Val Ile Ala Pro Arg Arg Leu Pro Asp Pro Gln Ile Leu Lys
1               5                   10                  15

Ser Asp Thr
```

```
<210> SEQ ID NO 4
<211> LENGTH: 12
<212> TYPE: PRT
<213> ORGANISM: Artificial Sequence
<220> FEATURE:
<223> OTHER INFORMATION: synthetic peptide

<400> SEQUENCE: 4

Pro Asp Ala Lys Thr Gln Cys Pro Asp Asp Ser Thr
```

<210> SEQ ID NO 5
<211> LENGTH: 14
<212> TYPE: PRT
<213> ORGANISM: Artificial Sequence
<220> FEATURE:
<223> OTHER INFORMATION: synthetic peptide

<400> SEQUENCE: 5

Ser Ala Arg Gly Thr Lys Cys Leu Arg Lys Lys Ile Pro Arg
1               5                   10

<210> SEQ ID NO 6
<211> LENGTH: 19
<212> TYPE: PRT
<213> ORGANISM: Artificial Sequence
<220> FEATURE:
<223> OTHER INFORMATION: synthetic peptide

<400> SEQUENCE: 6

Glu Lys Ala Pro Ala His Leu Ser Leu Pro Asp Pro Gln Ala Leu Lys
1               5                   10                  15

Arg Asp Val

<210> SEQ ID NO 7
<211> LENGTH: 14
<212> TYPE: PRT
<213> ORGANISM: Artificial Sequence
<220> FEATURE:
<223> OTHER INFORMATION: synthetic peptide

<400> SEQUENCE: 7

Ala Arg Arg Gly Thr Lys Cys Leu Arg Arg Glu Ala Pro Arg
1               5                   10

<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 8
cctacttggc agtacatcta cgta                                          24

<210> SEQ ID NO 9
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 9
cgagaattca ggcagaccat gtgggtc                                       27

<210> SEQ ID NO 10
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 10
cgagaattca ggcagaccat gtgggtc                                       27

```
<210> SEQ ID NO 11
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 11
ctgacggttc actaaacgag ctc                                                 23

<210> SEQ ID NO 12
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 12
ggatccacgg agttgttacc tgatc                                               25

<210> SEQ ID NO 13
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 13
gaattcgcag gcagaccatg tggac                                               25

<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 14
gggtccacat ggtctgcctg c                                                   21

<210> SEQ ID NO 15
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 15
gccaccagcc ctgctgttaa ggcc                                                24

<210> SEQ ID NO 16
<211> LENGTH: 2095
<212> TYPE: DNA
<213> ORGANISM: Homo sapiens

<400> SEQUENCE: 16
cgcaggcaga cc atg tgg acc ctg gtg agc tgg gtg gcc tta aca gca ggg        51
              Met Trp Thr Leu Val Ser Trp Val Ala Leu Thr Ala Gly
                1               5                  10 ctg gtg gct gga acg cgg tgc cca gat ggt cag ttc tgc cct gtg gcc          99
Leu Val Ala Gly Thr Arg Cys Pro Asp Gly Gln Phe Cys Pro Val Ala
 15                  20                  25 tgc tgc ctg gac ccc gga gga gcc agc tac agc tgc tgc cgt ccc ctt         147
Cys Cys Leu Asp Pro Gly Gly Ala Ser Tyr Ser Cys Cys Arg Pro Leu
 30                  35                  40                  45 ctg gac aaa tgg ccc aca aca ctg agc agg cat ctg ggt ggc ccc tgc         195
```

```
Leu Asp Lys Trp Pro Thr Thr Leu Ser Arg His Leu Gly Gly Pro Cys
            50              55                  60 cag gtt gat gcc cac tgc tct gcc ggc cac tcc tgc atc ttt acc gtc       243
Gln Val Asp Ala His Cys Ser Ala Gly His Ser Cys Ile Phe Thr Val
                65              70                  75 tca ggg act tcc agt tgc tgc ccc ttc cca gag gcc gtg gca tgc ggg       291
Ser Gly Thr Ser Ser Cys Cys Pro Phe Pro Glu Ala Val Ala Cys Gly
                80              85                  90 gat ggc cat cac tgc tgc cca cgg ggc ttc cac tgc agt gca gac ggg       339
Asp Gly His His Cys Cys Pro Arg Gly Phe His Cys Ser Ala Asp Gly
        95              100                 105 cga tcc tgc ttc caa aga tca ggt aac aac tcc gtg ggt gcc atc cag       387
Arg Ser Cys Phe Gln Arg Ser Gly Asn Asn Ser Val Gly Ala Ile Gln
110             115                 120                 125 tgc cct gat agt cag ttc gaa tgc ccg gac ttc tcc acg tgc tgt gtt       435
Cys Pro Asp Ser Gln Phe Glu Cys Pro Asp Phe Ser Thr Cys Cys Val
                130                 135                 140 atg gtc gat ggc tcc tgg ggg tgc tgc ccc atg ccc cag gct tcc tgc       483
Met Val Asp Gly Ser Trp Gly Cys Cys Pro Met Pro Gln Ala Ser Cys
                145                 150                 155 tgt gaa gac agg gtg cac tgc tgt ccg cac ggt gcc ttc tgc gac ctg       531
Cys Glu Asp Arg Val His Cys Cys Pro His Gly Ala Phe Cys Asp Leu
                160                 165                 170 gtt cac acc cgc tgc atc aca ccc acg ggc acc cac ccc ctg gca aag       579
Val His Thr Arg Cys Ile Thr Pro Thr Gly Thr His Pro Leu Ala Lys
        175                 180                 185 aag ctc cct gcc cag agg act aac agg gca gtg gcc ttg tcc agc tcg       627
Lys Leu Pro Ala Gln Arg Thr Asn Arg Ala Val Ala Leu Ser Ser Ser
190                 195                 200                 205 gtc atg tgt ccg gac gca cgg tcc cgg tgc cct gat ggt tct acc tgc       675
Val Met Cys Pro Asp Ala Arg Ser Arg Cys Pro Asp Gly Ser Thr Cys
                210                 215                 220 tgt gag ctg ccc agt ggg aag tat ggc tgc tgc cca atg ccc aac gcc       723
Cys Glu Leu Pro Ser Gly Lys Tyr Gly Cys Cys Pro Met Pro Asn Ala
                225                 230                 235 acc tgc tgc tcc gat cac ctg cac tgc tgc ccc caa gac act gtg tgt       771
Thr Cys Cys Ser Asp His Leu His Cys Cys Pro Gln Asp Thr Val Cys
                240                 245                 250 gac ctg atc cag agt aag tgc ctc tcc aag gag aac gct acc acg gac       819
Asp Leu Ile Gln Ser Lys Cys Leu Ser Lys Glu Asn Ala Thr Thr Asp
255                 260                 265 ctc ctc act aag ctg cct gcg cac aca gtg ggc gat gtg aaa tgt gac       867
Leu Leu Thr Lys Leu Pro Ala His Thr Val Gly Asp Val Lys Cys Asp
270                 275                 280                 285 atg gag gtg agc tgc cca gat ggc tat acc tgc tgc cgt cta cag tcg       915
Met Glu Val Ser Cys Pro Asp Gly Tyr Thr Cys Cys Arg Leu Gln Ser
                290                 295                 300 ggg gcc tgg ggc tgc tgc cct ttt acc cag gct gtg tgc tgt gag gac       963
Gly Ala Trp Gly Cys Cys Pro Phe Thr Gln Ala Val Cys Cys Glu Asp
                305                 310                 315 cac ata cac tgc tgt ccc gcg ggg ttt acg tgt gac acg cag aag ggt      1011
His Ile His Cys Cys Pro Ala Gly Phe Thr Cys Asp Thr Gln Lys Gly
        320                 325                 330 acc tgt gaa cag ggg ccc cac cag gtg ccc tgg atg gag aag gcc cca      1059
Thr Cys Glu Gln Gly Pro His Gln Val Pro Trp Met Glu Lys Ala Pro
335                 340                 345 gct cac ctc agc ctg cca gac cca caa gcc ttg aag aga gat gtc ccc      1107
Ala His Leu Ser Leu Pro Asp Pro Gln Ala Leu Lys Arg Asp Val Pro
350                 355                 360                 365 tgt gat aat gtc agc agc tgt ccc tcc tcc gat acc tgc tgc caa ctc      1155
```

```
Cys Asp Asn Val Ser Ser Cys Pro Ser Ser Asp Thr Cys Cys Gln Leu
            370                 375                 380 acg tct ggg gag tgg ggc tgc tgt cca atc cca gag gct gtc tgc tgc    1203
Thr Ser Gly Glu Trp Gly Cys Cys Pro Ile Pro Glu Ala Val Cys Cys
        385                 390                 395 tcg gac cac cag cac tgc tgc ccc cag cga tac acg tgt gta gct gag    1251
Ser Asp His Gln His Cys Cys Pro Gln Arg Tyr Thr Cys Val Ala Glu
            400                 405                 410 ggg cag tgt cag cga gga agc gag atc gtg gct gga ctg gag aag atg    1299
Gly Gln Cys Gln Arg Gly Ser Glu Ile Val Ala Gly Leu Glu Lys Met
        415                 420                 425 cct gcc cgc cgc ggt tcc tta tcc cac ccc aga gac atc ggc tgt gac    1347
Pro Ala Arg Arg Gly Ser Leu Ser His Pro Arg Asp Ile Gly Cys Asp
430                 435                 440                 445 cag cac acc agc tgc ccg gtg ggc gga acc tgc tgc ccg agc cag ggt    1395
Gln His Thr Ser Cys Pro Val Gly Gly Thr Cys Cys Pro Ser Gln Gly
            450                 455                 460 ggg agc tgg gcc tgc tgc cag ttg ccc cat gct gtg tgc tgc gag gat    1443
Gly Ser Trp Ala Cys Cys Gln Leu Pro His Ala Val Cys Cys Glu Asp
        465                 470                 475 cgc cag cac tgc tgc ccg gct ggc tac acc tgc aac gtg aag gct cga    1491
Arg Gln His Cys Cys Pro Ala Gly Tyr Thr Cys Asn Val Lys Ala Arg
            480                 485                 490 tcc tgc gag aag gaa gtg gtc tct gcc cag cct gcc acc ttc ctg gcc    1539
Ser Cys Glu Lys Glu Val Val Ser Ala Gln Pro Ala Thr Phe Leu Ala
        495                 500                 505 cgt agc cct cac gtg ggt gtg aag gac gtg gag tgt ggg gaa gga cac    1587
Arg Ser Pro His Val Gly Val Lys Asp Val Glu Cys Gly Glu Gly His
510                 515                 520                 525 ttc tgc cat gat aac cag acc tgc tgc cga gac aac cga cag ggc tgg    1635
Phe Cys His Asp Asn Gln Thr Cys Cys Arg Asp Asn Arg Gln Gly Trp
            530                 535                 540 gcc tgc tgt ccc tac gcc cag ggc gtc tgt tgt gct gat cgg cgc cac    1683
Ala Cys Cys Pro Tyr Ala Gln Gly Val Cys Cys Ala Asp Arg Arg His
        545                 550                 555 tgc tgt cct gct ggc ttc cgc tgc gca cgc agg ggt acc aag tgt ttg    1731
Cys Cys Pro Ala Gly Phe Arg Cys Ala Arg Arg Gly Thr Lys Cys Leu
            560                 565                 570 cgc agg gag gcc ccg cgc tgg gac gcc cct ttg agg gac cca gcc ttg    1779
Arg Arg Glu Ala Pro Arg Trp Asp Ala Pro Leu Arg Asp Pro Ala Leu
        575                 580                 585 aga cag ctg ctg tgagggacag tactgaagac tctgcagccc tcgggacccc       1831
Arg Gln Leu Leu
590 actcggaggg tgccctctgc tcaggcctcc ctagcacctc ccctaaccaa aattctccct    1891 ggaccccatt ctgagctccc catcaccatg ggaggtgggg cctcaatcta aggcccttcc    1951 ctgtcagaag ggggttgagg caaaagccca ttacaagctg ccatccctc cccgtttcag     2011 tggaccctgt ggccaggtgc ttttccctat ccacaggggt gtttgtgtgt tgggtgtgct    2071 ttcaataaag tttgtcactt tctt                                           2095

<210> SEQ ID NO 17
<211> LENGTH: 593
<212> TYPE: PRT
<213> ORGANISM: Homo sapiens

<400> SEQUENCE: 17

Met Trp Thr Leu Val Ser Trp Val Ala Leu Thr Ala Gly Leu Val Ala
1               5                   10                  15
```

```
Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Arg Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Gly Ser Leu Ser His Pro Arg Asp Ile Gly Cys Asp Gln His Thr
        435                 440                 445
```

```
Ser Cys Pro Val Gly Gly Thr Cys Cys Pro Ser Gln Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
    530                 535                 540

Pro Tyr Ala Gln Gly Val Cys Cys Ala Asp Arg Arg His Cys Cys Pro
545                 550                 555                 560

Ala Gly Phe Arg Cys Ala Arg Arg Gly Thr Lys Cys Leu Arg Arg Glu
                565                 570                 575

Ala Pro Arg Trp Asp Ala Pro Leu Arg Asp Pro Ala Leu Arg Gln Leu
                580                 585                 590

Leu
```